United States Patent
Anthony et al.

(10) Patent No.: US 11,744,877 B2
(45) Date of Patent: Sep. 5, 2023

(54) METHOD FOR PERMEABILIZING TUMOR VASCULATURE USING A TUMOR VASCULATURE PERMEABILIZING MOLECULE TO IMPROVE ACCESS OF A THERAPEUTIC OR DIAGNOSTIC AGENT TO A TUMOR

(75) Inventors: Daniel Anthony, Oxford (GB); Nicola Sibson, Oxford (GB); Len Seymour, Oxford (GB); Kerry Fisher, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 179 days.

(21) Appl. No.: 13/514,138

(22) PCT Filed: Dec. 8, 2010

(86) PCT No.: PCT/GB2010/052048
§ 371 (c)(1),
(2), (4) Date: Nov. 19, 2012

(87) PCT Pub. No.: WO2011/070358
PCT Pub. Date: Jun. 16, 2011

(65) Prior Publication Data
US 2013/0101550 A1    Apr. 25, 2013

(30) Foreign Application Priority Data
Dec. 8, 2010  (GB) .................................... 0921525

(51) Int. Cl.
*A61K 38/19*   (2006.01)
*A61K 45/06*   (2006.01)
*A61K 49/00*   (2006.01)

(52) U.S. Cl.
CPC ............ *A61K 38/191* (2013.01); *A61K 45/06* (2013.01); *A61K 49/0002* (2013.01)

(58) Field of Classification Search
CPC ......... A61K 38/191; A61P 35/00; A61P 35/04
See application file for complete search history.

(56) References Cited

U.S. PATENT DOCUMENTS

| | | | |
|---|---|---|---|
| 6,991,785 B2* | 1/2006 | Frey, II | 424/85.6 |
| 2007/0086942 A1 | 4/2007 | Chang et al. | |
| 2009/0048179 A1* | 2/2009 | Black | 514/15 |
| 2009/0246145 A1* | 10/2009 | Small | 424/9.361 |

FOREIGN PATENT DOCUMENTS

| | | |
|---|---|---|
| JP | 63170324 | 7/1988 |
| WO | 199308210 A1 | 4/1993 |
| WO | 199962315 A2 | 12/1999 |
| WO | 200013703 A2 | 3/2000 |
| WO | 200137859 A2 | 5/2001 |
| WO | 200154771 A2 | 8/2001 |
| WO | 2003028840 A2 | 4/2003 |
| WO | 2005053642 A1 | 6/2005 |
| WO | 2007146414 A2 | 12/2007 |
| WO | 2008107729 A1 | 9/2008 |
| WO | 2008119493 A1 | 10/2008 |
| WO | 2008144753 A2 | 11/2008 |

OTHER PUBLICATIONS

Kido et al. Acute effects of human recombinant tumor necrosis factor-a on the cerebral vasculature of the rat in both normal brain and in an experimental glioma model. J Neurooncol. Apr. 1991;10(2):95-109.*
Schneider et al. "Glioblastoma cells release factors that disrupt blood-brain barrier features". Mar. 2004, Acta Neuropathologica 107 (3): 272-276.*
Jain et al. Angiogenesis in brain tumours. Nat Rev Neurosci. Aug. 2007;8(8):610-22.*
Serres et al. Molecular MRI enables early and sensitive detection of brain metastases. Proc Natl Acad Sci U. S. A., Apr. 24, 2012, 109(17): 6674-6679.*
OMIM Entry—* 600978—Lymphotoxin-Beta; pp. 1-5. Accessed Mar. 14, 2016.*
Hagen et al. Low-Dose Tumor Necrosis Factor-a Augments Antitumor Activity of Stealth Liposomal Doxorubicin (DOXILt) in Soft Tissue Sarcoma-Bearing Rats. Int J Cancer. Sep. 15, 2000;87(6):829-37.*
Lejeune FJ. Clinical use of TNF revisited: improving penetration of anti-cancer agents by increasing vascular permeabilityJ Clin Invest. 2002; 110: 433-435.*
Pan et al. Tumor necrosis factor and stroke: role of the blood-brain barrier. Prog Neurobiol. Dec. 2007; 83(6): 363-374.*
Loetscher et al. Human Tumor Necrosis Factor a (TNFa) Mutants with Exclusive Specificity for the 55-kDa or 75-kDa TNF Receptors. J. Biol. Chem., 1993, 268 (36): 26360-26367.*
International Search Report and Written Opinion; International Application No. PCT/GB2010/052048; International Filing Date Dec. 8, 2010; dated Jun. 10, 2011; 26 pages.
Kido et al.; "Acute Effects of the Human Recombinant Tumor Necrosis Factor (rTNF) on the Cerebral Vasculature of the Rat in Both Normal Brain and an Experimental Glioma Model"; Biol. Aspects Brain Tumors, Proc. Nikko Brain Tumor Conf., 8th; Meeting Date 1990, pp. 221-228; Editors: Tabuchi, Kazuo; Publisher: Springer, Tokyo, Japan, 8 pages; (1991).

(Continued)

*Primary Examiner* — Dong Jiang
(74) *Attorney, Agent, or Firm* — CANTOR COLBURN LLP

(57) ABSTRACT

The present invention provides a tumour vasculature permeabilising molecule for use in permeabilising vasculature of a tumour for treating, detecting or diagnosing said tumour wherein said tumour vasculature permeabilising molecule is formulated for systemic administration to said patient. A composition comprising a tumour vasculature permeabilising molecule and an appropriate anticancer agent or imaging agent, and a method of treatment or a method of detecting the presence or absence of a tumour are also provided.

Figure 1:
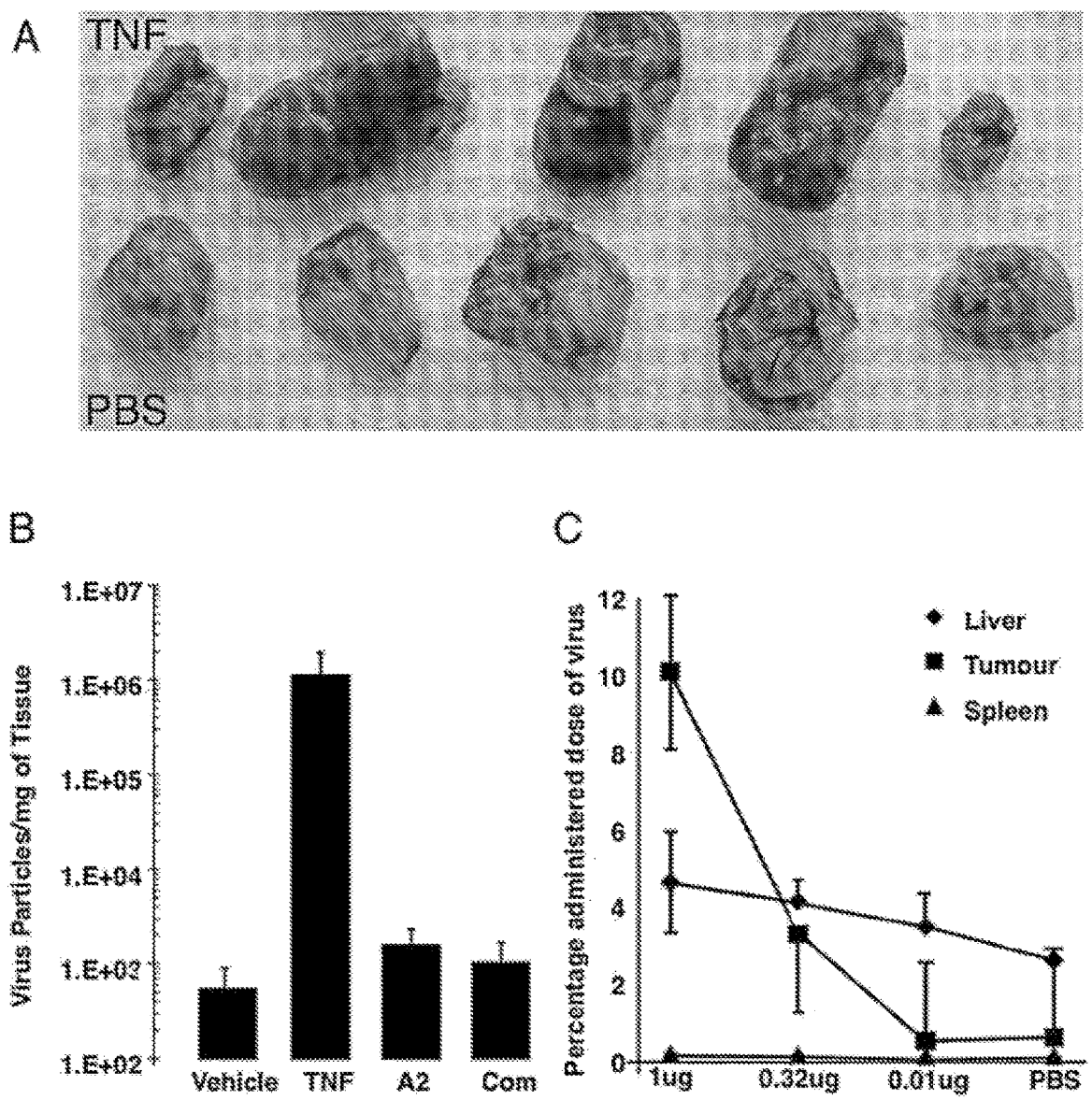

28 Claims, 3 Drawing Sheets
Specification includes a Sequence Listing.

(56) References Cited

OTHER PUBLICATIONS

Saija, et al.; "Systemic Cytokine Administration Can Affect Blood-Brain Barrier Permeability in the Rat"; Life Sciences; 56(10); pp. 775-784; (1995).
Wright et al.; "Effects of an Intratumoral Injection of Human Recombinant Tumor Necrosis Factor-a on Cerebrovascular Permeability and Leukocytic Infiltration in a Rat Glioma Model"; Acta Neuropathol; 93; pp. 78-86; (1997).
Aicher et al.; "Contrast-Enhanced Magnetic Resonance Imaging of Tumor-Bearing Mice Treated with Human Recombinant Tumor Necrosis Factor a1"; Cancer Research; 50; pp. 7376-7381; (1990).
Bazan-Peregrino et al.; "Comparison of Molecular Strategies for Breast Cancer Virotherapy Using Oncolytic Adenovirus"; Human Gene Therapy; 19; pp. 873-886; (2008).
Blamire et al.; "Interleukin-1B-Induced Changes in Blood-Brain Barrier Permeability, Apparent Diffusion Coefficient, and Cerebral Blood Volume in the Rat Brain: A Magnetic Resonance Study"; The Journal of Neuroscience; 20(21); pp. 8153-8159; (2000).
Broom et al.; "MRI Reveals that Early Changes in Cerebral Blood Volume Precede Blood-Brain Barrier Breakdown and Overt Pathology in MS-Like Lesions in Rat Brain"; Journal of Cerebral Blood Flow & Metabolism; 25; pp. 204-216; (2005).
Campbell et al.; "Altered Chemokine Expression in the Spinal Cord and Brain Contributes to Differential Interleukin-1 B-Induced Neutrophil Recruitment"; Journal of Neurochemistry; 83; pp. 432-441; (2002).
Campbell, et al.; "Loss of the Atypical Inflammatory Response in Juvenile and Aged Rats"; Neuropathology and Applied Neurobiology; 33; pp. 108-120; (2007).
Ferrero et al.; "Roles of Tumor Necrosis Factor p55 and p75 Receptors in TNF-alpha-Induced Vascular Permeability"; Am J Physiol Cell Physiol; 281; C1173-C1179; (2001).
UKIPO Search Report; GB0921525.2; dated Apr. 7, 2010; 2 pages.
JPS63-170324; Published Jul. 17, 1998; English Translation; 5 pages.
Lejeune et al., "Efficiency of Recombinant Human TNF in Human Cancer Therapy"; Cancer Immunity; 6; pp. 1-17 (2006).
Sibson et al.; "MRI Detection of Early Endothelial Activation in Brain Inflammation"; Magnetic Resonance in Medicine; 51; pp. 248-252; (2004).
Sibson et al.; "TNF-alpha Reduces Cerebral Blood Volume and Disrupts Tissue Homeostasis via an Endothelin- and TNFR2-Dependent Pathway"; Brain; 125; pp. 2446-2459; (2002).
Temming et al.; "RGD-Bsed Strategies for Selective Delivery of Therapeutics and Imaging Agents to the Tumour Vasculature"; Drug Resistance Updated; 8; pp. 381-402; (2005).
Von zur Muhlen et al.; "A Contrast Agent Recognizing Activated Platelet Reveals Murine Cerebral Malaria Pathology Undetectable by Conventional MRI"; The Journal of Clinical Investigation; 118(3); pp. 1198-1207 (2008).
Loetscher et al.; "Human Tumor Necrosis Factor a (TNFa) Mutants with Exclusive Specificity for the 55-kDa or 75-kDa TNF Receptors"; Journal of Biological Chemistry; 268(35) pp. 26350-26357; (1993).
Browning, et al.; "Characterization of Surface Lymphotoxin Forms. Use of Specific Monoclonal Antibodies and Soluble Receptors"; BioGRID Publication Summary; http://thebiogrid.org/5018/publication/characterization-of-surface- . . . ; also may be viewed in J.Immunol. Jan. 1, 1995; 154(1); pp. 33-46 (1995) [PUBMED:7995952].
Connell et al.; "Selective Permeabilization of the Blood-Brain Barrier at Sites of Metastasis"; JNCI; 105(21); pp. 1634-1643; (2013).
Carbonell et al.; "The Vascular Bsement Membrane as "Soil" in Brain Metastasis"; PLOS one; 4(6); e5857; 14 pages; (2009).
Katakami et al.; "Magnetic Resonance Evaluation of Brain Metastases from Systemic Malignances With Two Doses of Gadobutrol 1.0 M Compred With Gadoteridol"; Investigative Radiology; 46(7); pp. 411-418; (2011).
Nomoto et al.; "Brain Metastasis of Small Cell Lung Carcinoma: Comparison of Gd-DTPA Enhanced Magnetic Resonance Imaging and Enhanced Computerized Tomography"; Jpn J Clin Oncol; 24; pp. 258-262; (1994).
Milton, O. Lee; Determination of the Surface Area of the White Rat With Its Application to the Expression of Metabolic Results; Downloaded from www.physiology.org/journal/ajplegacy at Oxford Univ Bodleian Lib (129.067.117.158) on Apr. 5, 2019; 10 pages.
Mittelman et al.; "A Phase I Pharmacokinetic Study of Recombinant Human Tumor Necrosis Factor Administered by a 5-day Continuous Infusion"; Invest New Drugs; 1992; Aug. 10(3); pp. 183-190; abstract only; 2 pages.
Schiller et al.; "Biological and Clinical Effects of Intravenoue Tumor Necrosis Factor-alpha Administered Three Times Weekly"; Cancer Res.; Mar. 15, 1991; 51(6); pp. 1651-1658; abstract only; 2 pages.
Wiedenmann et al.; "Phase-I Trial of Intravenous Continuous Infusion of Tumor Necrosis Factor in Advanced Metastatic Carcinomas"; J Cancer Res Clin Oncol.; 1989; 115(2); pp. 189-192; abstract only; 1 page.
Gamm et al.; "Phase I Trial of Recombinant Human Tumour Necrosis Factor Alpha in Patients With Advanced Malignancy"; Eur J Cancer; 1991; 27(7); pp. 856-863; Abstract only; one page.
Fox, B. et al.; "Epidemiology of Metastatic Brain Tumors"; Neurosurgery Clinics of North America, vol. 22, Issue No. 1; 2011; 6 pages; doi: 10.1016/j.nec.2010.08.007.
Tabouret, E. et al.; "Recent Trends in Epidemiology of Brain Metastases: An Overview"; Anticancer Research, vol. 32, Issue No. 11; 2012; pp. 4655-4662.
Van Ostade, X.; "Human TNF mutants with selective activity on the p55 receptor"; Nature, vol. 361; 1993; pp. 266-269; DOI: https://doi.org/10.1038/361266a0.
Yamagishi, J. et al.; "Mutational analysis of structure—activity relationships in human tumor necrosis factor-alpha" Protein Engineering, vol. 3, Issue No. 8; 1990; pp. 713-719.

* cited by examiner

SEQUENCE LISTING

```
<160> NUMBER OF SEQ ID NOS: 2

<210> SEQ ID NO 1
<211> LENGTH: 233
<212> TYPE: PRT
<213> ORGANISM: human

<400> SEQUENCE: 1

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
            85                  90                  95
```

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
            115                 120                 125

Glu Gly Leu Tyr Leu Ile Tyr Ser Gln Val Leu Phe Lys Gly Gln Gly
            130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
            165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
            195                 200                 205

Ser Ala Glu Ile Asn Arg Pro Asp Tyr Leu Asp Phe Ala Glu Ser Gly
            210                 215                 220

Gln Val Tyr Phe Gly Ile Ile Ala Leu
225                 230

<210> SEQ ID NO 2
<211> LENGTH: 205
<212> TYPE: PRT
<213> ORGANISM: human

<400> SEQUENCE: 2

Met Thr Pro Pro Glu Arg Leu Phe Leu Pro Arg Val Cys Gly Thr Thr
1               5                   10                  15

Leu His Leu Leu Leu Leu Gly Leu Leu Leu Val Leu Leu Pro Gly Ala
            20                  25                  30

Gln Gly Leu Pro Gly Val Gly Leu Thr Pro Ser Ala Ala Gln Thr Ala
            35                  40                  45

Arg Gln His Pro Lys Met His Leu Ala His Ser Thr Leu Lys Pro Ala
50                  55                  60

Ala His Leu Ile Gly Asp Pro Ser Lys Gln Asn Ser Leu Leu Trp Arg
65                  70                  75                  80

Ala Asn Thr Asp Arg Ala Phe Leu Gln Asp Gly Phe Ser Leu Ser Asn
            85                  90                  95

Asn Ser Leu Leu Val Pro Thr Ser Gly Ile Tyr Phe Val Tyr Ser Gln
            100                 105                 110

Val Val Phe Ser Gly Lys Ala Tyr Ser Pro Lys Ala Thr Ser Ser Pro
            115                 120                 125

Leu Tyr Leu Ala His Glu Val Gln Leu Phe Ser Ser Gln Tyr Pro Phe
            130                 135                 140

His Val Pro Leu Leu Ser Ser Gln Lys Met Val Tyr Pro Gly Leu Gln
145                 150                 155                 160

Glu Pro Trp Leu His Ser Met Tyr His Gly Ala Ala Phe Gln Leu Thr
            165                 170                 175

Gln Gly Asp Gln Leu Ser Thr His Thr Asp Gly Ile Pro His Leu Val
            180                 185                 190

Leu Ser Pro Ser Thr Val Phe Phe Gly Ala Phe Ala Leu
            195                 200                 205

METHOD FOR PERMEABILIZING TUMOR VASCULATURE USING A TUMOR VASCULATURE PERMEABILIZING MOLECULE TO IMPROVE ACCESS OF A THERAPEUTIC OR DIAGNOSTIC AGENT TO A TUMOR

CROSS-REFERENCE TO RELATED APPLICATIONS

This application is a 371 of PCT/GB2010/052048 filed Dec. 8, 2010, which claims the benefit of priority to Great Britain Application No. 0921525.2, filed on Dec. 8, 2009; under the provisions of 35 U.S.C. 119 and the International Convention for the protection of Industrial Property, which are incorporated herein by reference.

The present invention relates to the use of a tumour vasculature permeabilising molecule in permeabilising tumour vasculature, which allows for improvements in the methods of both imaging and treating tumours, particularly central nervous system (CNS), including brain tumours. A composition comprising a tumour vasculature permeabilising molecule and an appropriate anticancer agent or imaging agent, and a method of treatment or a method of detecting the presence or absence of a tumour are also provided.

The prognosis for an individual diagnosed with a CNS tumour such as a brain tumour is not encouraging at present. Overall, for all types of brain tumours in adults, only 30% of patients live for at least a year after diagnosis. Both primary brain tumours and metastatic brain tumours are currently difficult to detect and to treat. In particular it is difficult to detect brain tumours when they are at a relatively early stage, i.e. when they are still very small. This is particularly important in relation to metastatic brain tumours since 20-40% of all cancer patients will suffer metastatic spread to the brain, and early intervention can be key to treating a patient successfully.

Detection of primary and metastatic CNS, including brain, tumours is presently limited. Imaging techniques play a central role in the diagnosis of brain tumours and non-invasive, high-resolution imaging techniques, such as computed tomography (CT) and especially magnetic resonance imaging (MRI) are used. It is advantageous when carrying out such imaging techniques to use a contrast agent. According to standard techniques, these contrast agents can access the CNS, including the brain, only when the tumour becomes sufficiently large (>5 mm) to cause gross structural abnormalities which in turn give rise to increases in blood brain barrier (BBB) permeability. The BBB, which effects the separation of cerebrospinal fluid and circulating blood, is maintained by tight junctions between the endothelial cells of central nervous system (CNS) blood vessels. Although endothelial cells of peripheral blood vessels also act to regulate the passage of molecules and cells from blood vessels, the barrier that is found around the CNS is particularly effective at restricting the passage of molecules and cells from CNS blood vessels and as such it is more difficult for a molecule to leave the circulation in the CNS, including the brain, than it is elsewhere in the body. As such it is only at later stages of tumour development, i.e. stages at which the tumour becomes sufficiently large to cause gross structural abnormalities which in turn give rise to increases BBB permeability that a contrast agent can reach the CNS, including the brain, from the vascular system and tumours can be revealed by imaging. Prior to this stage, contrast agents cannot be used since they cannot cross the BBB. Thus, it can be seen that it is very difficult to detect small tumours that are in the CNS and approaches to overcome the resistance of the BBB would represent an important advance to deliver more effective agents to the CNS.

While the early detection of small numbers of brain metastases will enable effective therapy, it is also clear that for some types of tumour it will inform a decision not to treat. For non-small cell lung carcinoma (NSCLC), 15.9% of patients eligible for thoracotomy could be excluded by upstaging due to the discovery of brain metastases and futile surgery would be avoided (S. Y. Kim et al, 2005, J Korean Med Sci 2005, 20:121-6). However, for those patients with <3 small brain metastases (current guidelines), radical therapy is an option and this will increase their life expectancy. If, say, life expectancy could be doubled from 6 months to 12, each patient would gain 0.33 QALYs. If radical therapy costs £3,000 ($10,350), this is a cost/QALY of £9,090 ($31,360), well within the definitions in the UK and USA for cost effective treatment. If 25% of patients with brain metastases can be successfully operated on, the collective gain to the original cohort of 100 patients is now 2.73 QALYs, with a cost saving of £32,000 ($444,700). By improving the ability to detect tumours at an early stage it may thus be possible to achieve, in combination with new therapies in development globally, a paradigm shift in health outcomes for patients.

Current therapy for CNS, including brain tumours includes radiotherapy, surgery and chemotherapy.

Radiotherapy is a standard treatment for patients with both primary CNS, including brain, tumours and metastases. Surgery may alternatively or additionally be used, in order to remove the whole or part of the tumour. However, the location of the tumour within the CNS may often preclude surgery and the key role of the CNS is such that it is not always possible to remove the whole tumour together with a safety margin of healthy tissue around it. As such, there may be an increased risk of recurrence associated with this type of treatment.

Chemotherapy may be used to help relieve symptoms in advanced brain tumours or in recurrent brain tumours, but it is difficult for most chemotherapy drugs to leave the vascular system and to penetrate the CNS to reach the cancer cells in the region of brain tumours since tumour vasculature in the brain is impermeable to most of these drugs as they do not, in most cases, cross the BBB readily. As such, most chemotherapeutics have lower activity in the CNS, including the brain, than they do at other sites of disease. For example the most active therapeutics for breast cancer (including doxorubicine, the taxanes and trastuzumab) appear not to reach the CNS in sufficient concentrations to be effective against secondary cancer in the brain resulting from primary breast cancer and very few chemotherapy trials have been reported for breast cancer brain metastases. CMF (cyclophosphamide, methotrexate, and fluorouracil) and PE (cisplatin and etoposide) regimes have been used, but the median survival of six months is similar to radiotherapy. Some attempts to avoid this problem have been made; drugs can be administered intrathecally, such as methotrexate. Alternatively, chemotherapy implants can be inserted directly into the brain, usually after surgery, but it can be seen from the above that currently the therapy of CNS, including brain, tumours is limited and that improved methods of treating such tumours are required.

It can be seen from the above discussions that both the detection or diagnosis of and the treatment of CNS, including brain, tumours would benefit from improving access of agents (e.g. therapeutic such as anticancer agents or signal generating agents such as imaging agents) to tumours in the CNS. The ability to detect CNS tumours at an earlier stage than is presently possible would clearly improve the chances of successful treatment, and in turn improving the treatment itself would be beneficial.

It is also clear that therapies and methods of detecting or diagnosing solid tumours elsewhere in the body other than the CNS (referred to herein as peripheral tumours) would also benefit from improvements. Improvements would be of relevance to peripheral tumours since improving access of agents (e.g. therapeutics such as anticancer agents or signal generating agents such as imaging agents) to all tumours would have the desirable effects of allowing reduced amounts of anticancer agents to be used in a treatment regime, and of improving detection and hence diagnosis of tumours. The advantage of improving detection of tumours has particular importance in the detection of secondary or metastatic tumours since the ability to detect such tumours at an earlier stage than is presently possible would clearly improve the chances of successful treatment.

Surprisingly, the inventors have observed that it is possible to increase the permeability of tumour vasculature in the region surrounding a tumour by the systemic administration of a tumour vasculature permeabilising molecule (e.g. TNF, (tumour necrosis factor, which was previously referred to as TNFα)). This increase in permeability has furthermore been shown to be specific to the region surrounding the tumour, i.e. it is a local effect, and it is also transient, since permeability has also been shown to return to normal levels subsequent to discontinuing the administration of the tumour vasculature permeabilising molecule.

This important and surprising observation has allowed the inventors to develop new and advantageous methods of treating or detecting (e.g. imaging) tumours. These methods take advantage of the fact that by increasing the permeability of tumour vasculature in the region surrounding a tumour, agents such as therapeutic agents (e.g. anticancer agents) or signal generating agents (e.g. imaging agents) will be able to leave the vascular system more readily in the region of the tumour. Since the access of the relevant agent to the tumour is improved, this also improves the ability of the agent to perform its function in therapy of the tumour or in the imaging or detection thereof.

The principles underlying the invention were demonstrated in mice bearing subcutaneous EL4 tumour xenografts, where the accumulation of proteins from the bloodstream (visualised by intravenous injection of Evans Blue dye) was dramatically increased by intravenous injection of 1 µg of human recombinant TNF (FIG. 1A). Similarly, the uptake of intravenously administered adenovirus particles can be increased by three orders of magnitude in this way (FIG. 1B).

At the time of the invention, direct stereotaxic injection of high concentrations of TNF was shown to have remarkably little effect on permeability of the normal brain endothelium (Sibson et al Brain, 2002; 125(Pt 11):2446-59). Furthermore it had been observed that TNF had no effect on the permeability of the BBB when administered systemically to normal animals. It was therefore assumed that TNF did not affect the BBB in either normal animals or those with a CNS, e.g. brain, tumour. However, as mentioned above, the inventors have observed that TNF, when administered systemically to animals with a brain tumour affects the BBB. This could not have been predicted from the literature given the unique characteristics of the brain vasculature. Furthermore, various effects have been described for TNF in the literature and the direct effects of this molecule on immune responses are often confused with the indirect effects that result from these immune responses.

Figure 4:
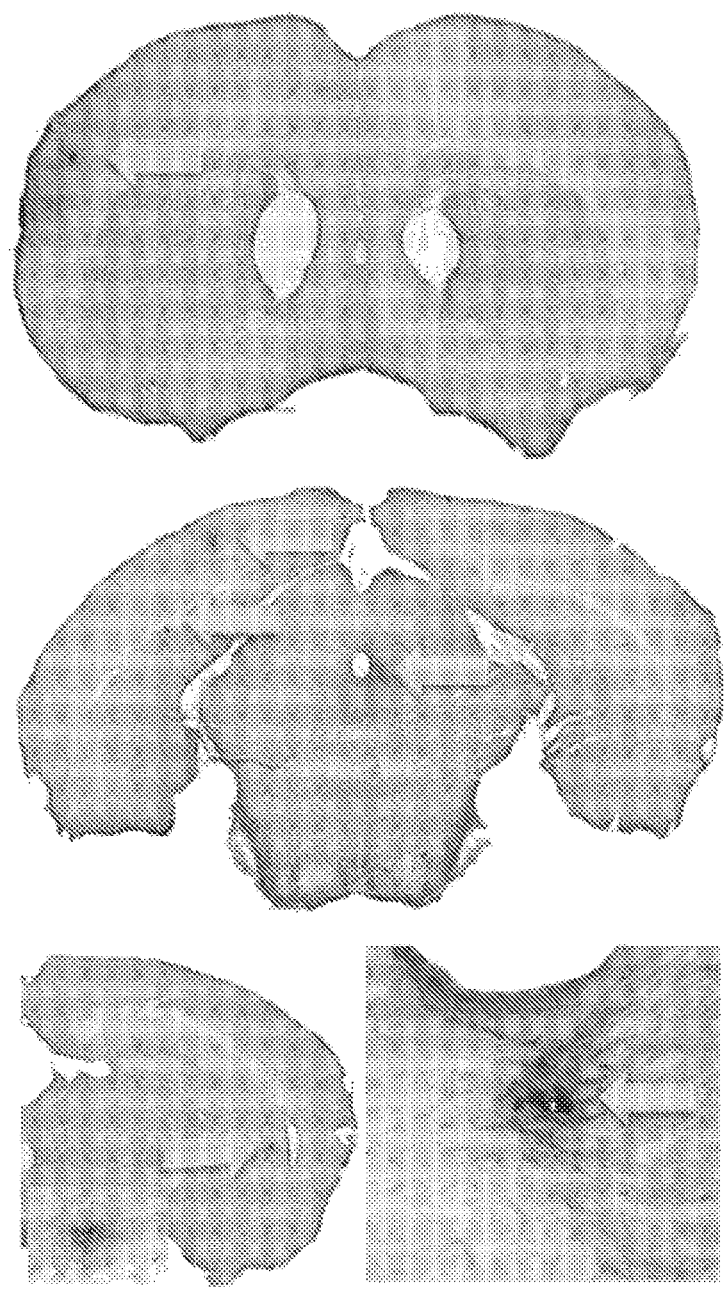

In a mouse model of brain metastasis, it was further shown that the tumour-associated endothelium in the murine brain metastasis model responds to TNF, but the normal vasculature does not (FIG. 4). Two hours after the systemic injection of TNF focal breakdown of the BBB was observed, which was not evident in controls or at 24 hours after intravenous TNF administration.

It is an important and surprising observation that the effects resulting from TNF administration are seen at levels which are much lower than the levels which have previously been suggested for use in the treatment of peripheral tumours, based on the cytotoxic effect of TNF. It is noteworthy that Phase I studies have reported a maximum tolerable dose (MTD) of 500 µg/m$^2$ for TNF, but this dose is not sufficiently high to achieve a cytotoxic effect and produce regression of tumours. Although TNF has been shown to have effects on tumour regression, this was only seen in mice at a concentration 10-fold higher than this, and hence beyond the MTD for TNF. It has now been found that levels up to the MTD are, however, comparable to the level of TNF that produces increases in tumour vessel permeability local to tumours and would facilitate the delivery of chemotherapy or signal generating agents. As such, the present invention does not require doses of TNF that exceed the MTD to be used and TNF can be used at doses which do not cause the problematic effects associated with administration of high concentrations of TNF. TNF is now used in isolated limb perfusions (ILP) at concentrations where the TNF is cytotoxic to the tumours, but too high to be tolerated systemically (Lejeune et al 2006 Cancer immunity 6:6).

It is an important and surprising observation that systemic administration of a tumour vasculature permeabilising molecule has no effect on normal vasculature, and the effect is thus specific to tumour vasculature (i.e. vasculature that is within, associated with, close to or adjacent to a tumour). As such, any agent (therapeutic or diagnostic) that is also administered to the patient at an appropriate time will tend to leave the vascular system in a much higher amount or concentration in the region of the tumour or surrounding the tumour, than elsewhere in the patient. This has the clear advantage that the agent will be likely to be present at higher concentrations in the regions in which its effect is desired, and will tend to be present at lower concentrations or be absent elsewhere in the patient. Furthermore, a generalised increased in vascular permeability is not desirable and would be likely to be associated with unwanted side effects. Whilst this is a clear advantage for tumours that occur throughout the body, this is particularly so in relation to the areas behind the BBB; the presence of the BBB is known to be key to protecting the brain, e.g. from bacterial infections. It is clear that a generalised breakdown of the BBB would compromise this protection and lead to unwanted side effects. This is clearly not desirable.

Similarly, the observation made by the inventors that the effect of systemic administration of a tumour vasculature permeabilising molecule on tumour vasculature is transient, such that normal levels of permeability of the tumour vasculature are restored subsequent to discontinuing the administration of the tumour vasculature permeabilising molecule (e.g. TNF) is also both important and surprising. In this way, as long as the agent of interest (e.g. the therapeutic or signal generating agent) is also present in the vasculature during the period of time in which vascular permeability is increased, it will be possible for the agent to pass through the relevant blood vessel wall resulting in it being present at higher concentrations in the regions in which its effect is desired. Clearly, it is advantageous for the vascular permeability to be increased only for as long as is necessary to facilitate or ensure the access of the agent to the tumour, and prolonged or generalised increases in vascular permeability would not be desirable. The restoration of normal levels of permeability of the tumour vasculature will thus also act to reduce or prevent unwanted side effects of the methods discussed herein.

It is further surprising that this observed effect of increased permeability of tumour vasculature is observed both in the tumour vasculature of tumours found in the body's periphery and also in the tumour vasculature that is present in brain tumours, and demonstrates that it is possible to increase the permeability of all tumour vasculature by systemic delivery of a tumour vasculature permeabilising molecule. The fact that increased permeability of tumour vasculature behind or beyond the BBB (e.g. in the brain) follows systemic administration of a tumour vasculature permeabilising molecule demonstrates that it is possible to increase the permeability of the BBB and thus allows the new and advantageous methods of treating or detecting and imaging tumours discussed above to be applied to tumours that are located behind or beyond the BBB. This is particularly advantageous in view of the fact that it has previously proved so difficult for agents such as therapeutic agents (e.g. anticancer agents) or signal generating (e.g. imaging) agents to access tumours that are behind the BBB prior to tumour induced breakdown of the BBB, by which time the tumours are very large.

The above observations thus provide a mechanism for increasing delivery of a range of therapeutic and imaging agents to tumours, including both peripheral tumours and tumours that are behind the BBB, thereby providing improved methods for treating and imaging said tumours.

Whilst not wishing to be bound by theory, the observed selective and transient increases in permeability of the tumour vasculature may result directly from differences in the expression patterns of receptors for the tumour vasculature permeabilising molecule (which in the case of the tumour vasculature permeabilising molecule TNF are TNFR-1 and TNFR-2) in the tumour vasculature when compared to normal or non-tumour vasculature, such that the tumour vasculature has the ability to respond to the tumour vasculature permeabilising molecule by activating signalling pathways via these receptors.

The present invention thus provides in a first embodiment a tumour vasculature permeabilising molecule for use in permeabilising tumour vasculature for treating, detecting or diagnosing said tumour wherein said tumour vasculature permeabilising molecule is formulated for systemic administration to said patient.

The term "vasculature" refers to any part of the circulatory system in an animal, i.e. to a blood vessel, which is any vessel (preferably a tubular vessel) conveying blood. This may be for example an artery, arteriole, vein, capillary or venule. All blood vessels contain endothelial cells.

Solid tumours, like any other tissue, require a functioning vasculature in order for the nutrients that they require for growth to be delivered and for waste products to be removed. If adequate vasculature is not present in the region of a tumour, a growing tumour will thus develop its own vasculature. Such vasculature (which can be described as a vascular network) can be acquired by the tumour at least in part, by the incorporation of existing host blood vessels, but may also involve the formation of new blood vessels, in processes known as angiogenesis and neovascularisation.

Tumour vasculature as referred to herein is thus any vasculature that is found within, in contact with, or associated with (near to or adjacent to) a solid tumour. Vasculature that is within a solid tumour is thus inside the solid tumour, i.e. surrounded by tumour or tumour tissue or cells. Vasculature that is in contact with a solid tumour may be within the tumour and/or may be at the tumour surface or periphery. Vasculature that is associated with a solid tumour may also be within or in contact with the tumour, but it also includes vasculature that is not directly in contact with the solid tumour, but is near to or adjacent to the tumour, e.g. within 10, 5, 3, 2 or 1 mm radius of any cells of the tumour mass. Tumour vasculature can thus be distinguished from normal or non-tumour vasculature on the basis of the location of the vasculature within an individual Tumour vasculature is thus sufficiently close to a tumour such that when said vasculature becomes permeabilised, access of agents present in the blood in said tumour vasculature is improved such that higher concentrations of such agents can reach said tumour.

Tumour vasculature can also be distinguished from normal or non-tumour vasculature on the basis of one or more cellular markers that may or may not be present in the relevant blood vessel e.g. in the cells (e.g. endothelial cells) that make up or form part of the relevant blood vessel. In other words, the proteins and other molecules that are found within and on the surface of the cells that make up the blood vessel may be different in tumour vasculature and normal or non-tumour vasculature. These molecules are referred to herein as tumour vasculature markers and the presence or absence of one or more of these markers or a group of these markers can be used to distinguish tumour vasculature from normal or non-tumour vasculature. Tumour vasculature thus contains a different pattern of markers compared to normal or non-tumour vasculature, or a different expression profile of markers compared to normal or non-tumour vasculature.

Markers that are found in tumour vasculature and not in normal or non-tumour vasculature are thus referred to herein as tumour vasculature makers. Markers that are found at higher levels (e.g. at least 1.1, 1.25, 2, 2.5, 3, 5, 10, 20, 50, 100 or 1000 fold higher levels) in tumour vasculature than in normal or non-tumour vasculature are considered to be tumour vasculature markers. Markers that are found in normal or non-tumour vasculature and not in tumour vasculature are thus referred to herein as normal or non-tumour vasculature makers. Markers that are found at higher levels (e.g. at least 1.1, 1.25, 2, 2.5, 3, 5, 10, 20, 50, 100 or 1000 fold higher levels) in normal or non-tumour vasculature than in tumour vasculature are considered to be normal or non-tumour vasculature markers.

These markers may be proteins, glycoproteins or polypeptides (which may be adhesion molecules, enzymes, receptors, signalling molecules, structural proteins, proteins involved in immune responses, proteins involved in the cell cycle) polysaccharides, nucleic acid molecules, lipids (e.g. phospholipids, glycolipids or other components of the plasma membrane). Such markers may be found at the surface of the relevant cell (e.g. within, attached to or associated with the cell membrane), or may be found within the relevant cell. Such markers can be detected, and if necessary quantitated using standard techniques that are well known in the art.

Figure 2:
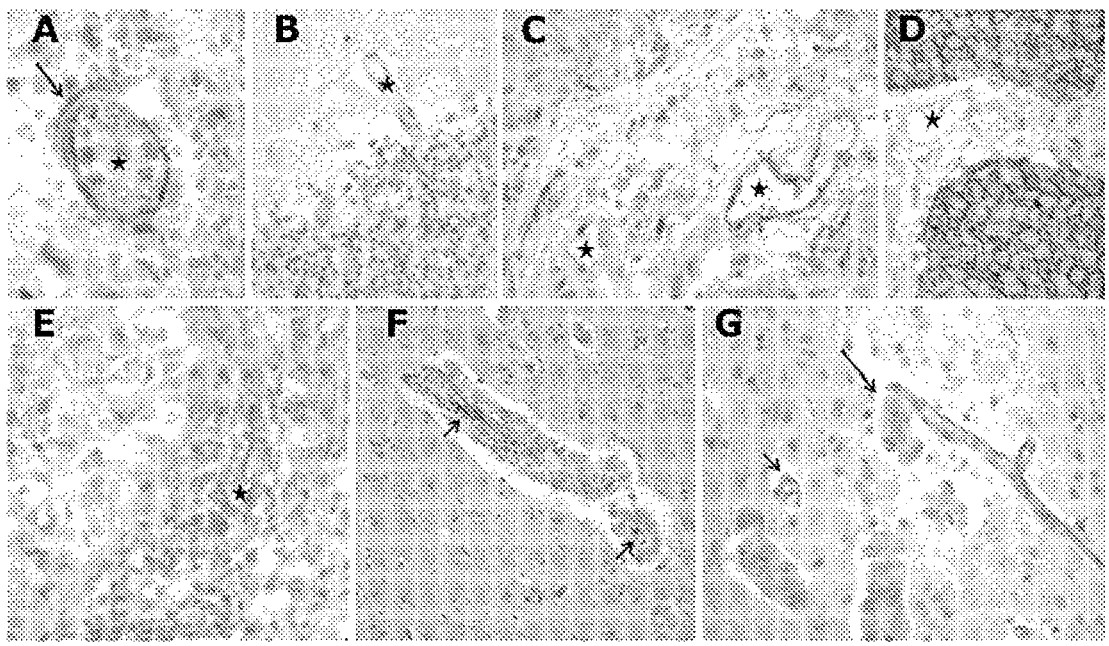
Figure 3:
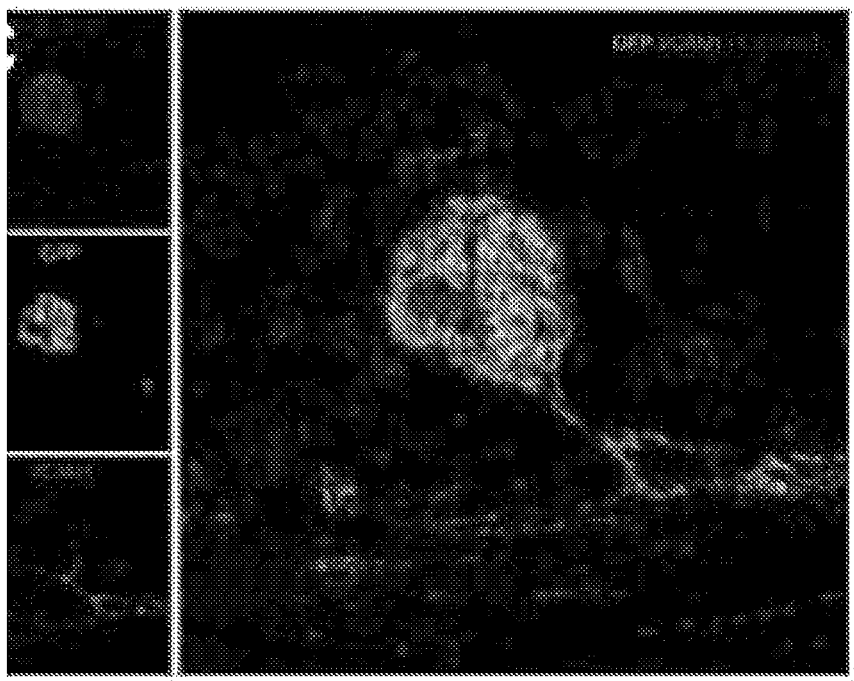

For example it has been shown that tumour vasculature in the brain expresses adhesion molecules and receptors which are not expressed by the normal brain endothelium (see FIGS. 2 and 3). Whilst these differences may in part account for the different behaviour of tumour vasculature compared to normal or non-tumour vasculature in terms of the observed responses to TNF, it can also be used as a way to distinguish tumour vasculature from normal or non-tumour vasculature.

Examples of molecules that are found in tumour vasculature and not in normal or non-tumour vasculature or at higher levels in tumour vasculature than in normal or non-tumour vasculature (tumour vasculature markers) include adhesion molecules such as vascular cell adhesion molecule-1 (VCAM-1), Inter-Cellular Adhesion Molecule 1 (ICAM) and selectins (e.g. P, E and L selectin) as well as active transport molecules such as the multidrug resistance transporter.

Molecules may also be found in normal or non-tumour vasculature and not in tumour vasculature or at higher levels in normal or non-tumour vasculature than in tumour vasculature (normal or non-tumour vasculature markers).

Thus, as alternatively defined, tumour vasculature is vasculature that expresses one or more of the tumour vasculature markers as defined above (or a group of such markers), or does so at a higher level (a statistically significantly higher level) than normal or non-tumour vasculature. Tumour vasculature can also be defined as vasculature that does not express one or more of the normal or non-tumour vasculature markers as defined above (or a group of such markers), or does so at a lower level (a statistically significantly lower level) than normal or non-tumour vasculature. The presence or absence or level of one of these markers can be used as an indication of whether vasculature is tumour vasculature as defined herein, or alternatively this assessment can be made of the basis of the presence or absence or level of at least 2, 3, 4, 5, 6, 7, 8, 9, 10, 20, 30, 40, 50 or 100 such markers.

As discussed elsewhere herein, systemic administration of a tumour vasculature permeabilising molecule has been shown by the present inventors to cause a selective and transient increase in permeability of the tumour vasculature, and as such tumour vasculature may also be distinguished from normal or non-tumour vasculature on this basis. Tumour vasculature may therefore be alternatively defined as vasculature which responds to systemic administration of a tumour vasculature permeabilising molecule (e.g. human TNF as described herein) in an individual, by showing increased vascular permeability compared to tumour vasculature in an individual which has not been subjected to systemic administration of a tumour vasculature permeabilising molecule or by showing increased permeability compared to normal or non-tumour vasculature in the same individual or in another individual who has been subjected to systemic administration of a tumour vasculature permeabilising molecule. Methods for determining this are discussed in more detail below.

The invention thus relates to permeabilising tumour vasculature, or alternatively stated to increasing the permeability of tumour vasculature.

Vascular permeability characterizes the capacity of a blood vessel (e.g. the blood vessel wall) to allow for the flow of small molecules (ions, water, nutrients), large molecules (e.g., proteins and nucleic acids) or whole cells in and out of the vessel. This passage of fluid, molecules and cells in and out of blood vessels is regulated in part by cell-cell adhesions between endothelial cells and the endothelial cell monolayer lining the vasculature forms a barrier that maintains the integrity of the blood fluid compartment, but permits passage of soluble factors and leukocytes in a regulated manner. In normal physiological processes, changes (e.g. increases or decreases) in vascular permeability may occur as a precisely regulated function, for example in immune responses and wound healing. Permeabilising tumour vasculature thus refers to causing an increase in tumour vascular permeability. This means that there is an increase in the number or type of molecules or cells that can move in or out of the relevant blood vessel, i.e. more molecules or cells can move in or out of the relevant blood vessel.

This increase may reflect the fact that the total number of molecules or cells that can move in or out of the relevant blood vessel is increased (i.e. more molecules or cells of all types can move in or out of the relevant blood vessel). Alternatively, the increase may be specific to one type of molecule or cell (e.g. one of small molecules (ions, water, nutrients), large molecules (e.g., proteins and nucleic acids) or whole cells) or to a certain small molecule, ion, nutrient, large molecule, protein, nucleic acid or group thereof. If the increase in permeability is specific to one type of molecule or cell or to a certain small molecule, or group thereof, in that one type of molecule or cell or a certain small molecule, or group thereof can pass more readily through the tumour vasculature than another type of molecule or cell or a certain small molecule, or group thereof, it can be defined as being a selective increase. Such a selective increase may reflect the fact that molecules sharing a certain property (e.g. molecules of a certain charge, size etc.) can move in or out of the relevant blood vessel more readily.

Alternatively or additionally any increase in permeability may reflect not only the number or nature of molecules or cells passing more readily through the tumour vasculature, but may reflect an increase in the number of blood vessels which are becoming permeabilised to the molecules.

As discussed above, the aim of the methods of the invention is to increase the access of agents such as signal generating, e.g. imaging agents and therapeutic, e.g. anticancer agents to tumours and as such in a preferred embodiment therefore the invention thus relates to increasing the permeability of tumour vasculature to signal generating, e.g. imaging and anticancer agents. Preferably said increase in the permeability of tumour vasculature is selective for said imaging and anticancer agents.

Any increase in the permeability of tumour vasculature is preferably statistically significant. To determine this, to the extent that this can be quantitated, the permeability of tumour vasculature following appropriate systemic treatment with a tumour vasculature permeabilising molecule as defined herein can be determined and compared to the permeability of tumour vasculature in the absence of such treatment, or to the permeability of normal or non-tumour vasculature following appropriate systemic treatment with a tumour vasculature permeabilising molecule. The increases referred to above may be at least 1.1, 1.25, 2, 2.5, 3, 5, 10, 20 fold.

The permeability of tumour vasculature can be measured functionally by administering an imaging agent as defined herein to an individual and observing the ability of this agent to pass through the tumour vasculature, e.g. by MRI, or as described in the Examples, e.g. by observing the ability of a blood borne or intravascular dye (such as Evans blue or FITC) or a radiolabelled compound (such as inulin or mannitol) to pass through the tumour vasculature in the presence and absence of an appropriate tumour vasculature permeabilising molecule. In other words it can readily be determined whether an increase in tumour vascular permeabilisation has occurred following systemic administration of an appropriate tumour vasculature permeabilising molecule, based on detecting the effect of the administration of this molecule on the ability of appropriate agents to pass through the tumour vasculature.

Alternatively defined, the process of permeabilising tumour vasculature can be defined as disrupting the integrity of the normal barrier surrounding said tumour vasculature. As discussed above, vasculature contains endothelial cells and it is these endothelial cells which are primarily responsible for controlling the movement of molecules and cells out of the vasculature. There is thus a barrier around all vascular cells and when said barrier around said tumour vasculature is intact, there is limited potential for movement of molecules and cells as referred to above from the vasculature into the tumour (e.g. the tumour in which the relevant blood vessel is found, is in contact with or with which the blood vessel is associated). When the relevant tumour vasculature permeabilising molecule is present systemically, the integrity of the barrier around the tumour vasculature is disrupted and the movement of molecules and cells as referred to above from the vasculature into the tumour can occur more readily or is increased, as discussed above.

When the tumour is in the brain, the barrier as referred to above is the BBB and as such in a preferred embodiment the systemic administration of a tumour vasculature permeabilising molecule causes the disruption of the integrity of the BBB.

As discussed above, tumour vasculature has been shown in the experimental systems used in the present Examples to respond differently to normal or non-tumour vasculature when a tumour vasculature permeabilising molecule is systemically administered to an individual, in that the permeability of tumour vasculature is increased whereas that of normal or non-tumour vasculature is not.

Whilst there is preferably no change to the permeability of normal or non-tumour vasculature following systemic administration with a tumour vasculature permeabilising molecule, some changes to the permeability of normal or non-tumour vasculature following systemic administration with a tumour vasculature permeabilising molecule would be tolerable, and are not excluded.

In a preferred embodiment therefore the effect of the tumour vasculature permeabilising molecule is specific to tumour vasculature. By specific it is meant that the permeabilisation effect of the tumour vasculature permeabilising molecule is observed only in tumour vasculature and not in normal or non-tumour vasculature, or that the permeabilisation effect of the tumour vasculature permeabilising molecule is observed to a greater extent in tumour vasculature than in normal or non-tumour vasculature. In other words the effect of the tumour vasculature permeabilising molecule on the permeability of the tumour vasculature is greater than the effect of the tumour vasculature permeabilising molecule on the permeability of normal or non-tumour vasculature. To the extent that this can be quantitated, the effect of the tumour vasculature permeabilising molecule on the permeability of the tumour vasculature is at least 1.1, 1.25, 2, 2.5, 3, 5, 10 or 20 fold greater than the effect of the tumour vasculature permeabilising molecule on the permeability of normal or non-tumour vasculature.

As discussed above, this has the advantages of avoiding generalised increases in vascular permeability which are undesirable.

As discussed above, the permeability of tumour vasculature has been shown experimentally in the Examples referred to herein to return to normal levels following the discontinuation of the systemic administration of a tumour vasculature permeabilising molecule to an individual.

In a preferred embodiment therefore the permeability of tumour vasculature increases only transiently, temporarily or reversibly. In other words the permeability of tumour vasculature returns to normal or substantially normal levels after the systemic administration of tumour vasculature permeabilising molecule to an individual is discontinued, i.e. after the administration of the tumour vasculature permeabilising molecule is stopped, withdrawn or ceased.

A normal level of permeability of tumour vasculature as referred to herein can be the level of permeability of tumour vasculature in the absence of any treatment with tumour vasculature permeabilising molecule, or the level of permeability of normal or non-tumour vasculature following treatment with a tumour vasculature permeabilising molecule. Substantially normal levels of permeability of tumour vasculature are thus approximately normal levels of tumour vasculature permeability, e.g. 0.9-1.1, 0.95-1.05, 0.975-1.025 fold that of tumour vasculature in the absence of any treatment with tumour vasculature permeabilising molecule, or of normal or non-tumour vasculature following treatment with a tumour vasculature permeabilising molecule, to the extent that this can be quantitated In a preferred embodiment therefore the effect of the tumour vasculature permeabilising molecule is transient and the permeability of tumour vasculature returns to substantially normal levels within 48, 36 or 24 hours, preferably within 23, 22, 21, 20, 19, 18, 17, 16, 15, 14, 13, 12, 11, 10, 9, 8, 7 or 6 hours after the systemic administration of a tumour vasculature permeabilising molecule to an individual is discontinued, withdrawn or ceased. Alternatively stated, the permeability of tumour vasculature returns to substantially normal levels within 6-24, 7-23, 8-22, 9-21, 10-20, 11-19, 12-18, 13-17, 14-16 hours after the systemic administration of a tumour vasculature permeabilising molecule to an individual is discontinued, withdrawn or ceased.

As discussed above, this has the advantages of avoiding prolonged increases in vascular permeability, which are undesirable. As long as any agent which is desired to reach the tumour is in the vascular system during the period in which the permeability of the tumour vasculature is increased, the agent will be able to pass through the tumour vasculature and reach the tumour to carry out the desired effects.

As referred to herein any molecule that acts on the tumour vasculature to increase the permeability thereof, when administered systemically to an individual, is a tumour vasculature permeabilising molecule according to the present invention. The effect is preferably specific to the tumour vasculature and transient, as discussed elsewhere herein.

It can readily be determined whether a molecule is a tumour vasculature permeabilising molecule by administering the molecule systemically to an individual having a tumour and determining whether the molecule has any effect on the permeability of the tumour vasculature, using methods as set out in the Examples and/or discussed elsewhere herein.

To the extent that this can be quantitated, following appropriate systemic treatment with a tumour vasculature permeabilising molecule, the permeability of tumour vasculature can be determined and compared to the permeability of tumour vasculature in the absence of such treatment, or to the permeability of normal or non-tumour vasculature following appropriate systemic treatment with a tumour vasculature permeabilising molecule. A tumour vasculature permeabilising molecule will preferably cause an increase in the permeability of tumour vasculature of at least 1.1, 1.25, 2, 2.5, 3, 5, 10 or 20 fold.

Preferred tumour vasculature permeabilising molecules are proinflammatory cytokines, including their variants, derivatives, truncated versions or mimetics thereof. A cytokine is a signalling molecule of the immune system, or an immunomodulating agent. Cytokines are secreted proteins, peptides, or glycoproteins and they may act in an autocrine or paracrine manner. By "proinflammatory cytokine" it is meant any cytokine that promotes an inflammatory response. This can be tested readily in vitro or in vivo using techniques known in the art, such as by determining whether a given molecule causes a macrophage in vitro to increase expression of one or more other proinflammatory cytokines such as IL-1, TNF, IL-12, IL-17, lymphotoxin α (LTα), lymphotoxin β (LTβ), IL-18, IL-6. Any change in expression of such molecules can be detected by detecting the protein product (e.g. using ELISA) or by detecting changes at the level of transcription (e.g. by RT-PCR or other techniques). This effect, as well as other functional effects of proinflammatory cytokines is inhibited by administration of the molecule IL-10. As such a "proinflammatory cytokine" is a cytokine that promotes an inflammatory response, which response can be inhibited by IL-10.

Examples of proinflammatory cytokines include IL-1, TNF, IL-12, IL-17, lymphotoxin α (LTα), lymphotoxin β (LTβ), IL-18, IL-6.

Preferred are molecules such as proinflammatory cytokines which encompasses their variants, derivatives, truncated versions (portions) or mimetics thereof that bind to the TNF receptor TNFR-1 and/or TNFR-2 (Aggarwal S, et al., J. Immunol. 1999; 162(4):2154-61). Particularly preferred are molecules such as proinflammatory cytokines including their variants, derivatives, truncated versions or mimetics thereof that bind to TNFR1. Preferred molecules, such as proinflammatory cytokines, including their variants, derivatives, truncated versions or mimetics thereof bind to the TNF receptor TNFR-1 and/or TNFR-2 in vivo and in vitro.

TNFR-1 is alternatively known as TNFRSF1A, CD120a, p55TNFR, TNF-R55, p60, TNF-R-I, TNFAR and TNFRβ.

TNFR-2 is alternatively known as TNFRSF1B, CD120b, p75TNFR, TNF-R75, p80, TNF-R-II, TNFBR and TNFRα.

These receptors are well characterised as being the receptors to which TNF binds in vivo and the receptors have been cloned and sequenced from various organisms. Such sequences are publicly available. The TNF receptors as referred to herein may be from any organism but are preferably mammalian e.g. from human, primate, rodent (e.g. rabbit, mouse, rat), especially preferably human.

Since proinflammatory cytokines exert their biological effects by virtue of binding to the appropriate receptor(s), it is clear that for an effect to be observed in a patient, the relevant molecule such as the proinflammatory cytokine, including a variant, derivative, truncated version or mimetic thereof must have the ability to bind to the appropriate receptor that is endogenously present in the tumour vasculature of that patient. As such, for the treatment of a human patient, the molecule such as the proinflammatory cytokine or variant, derivative truncated version or mimetic thereof must have the ability to bind to a human TNF receptor as defined herein, and similarly for the treatment of a mouse patient the molecule such as the proinflammatory cytokine or variant, derivative, truncated version or mimetic thereof must have the ability to bind to a mouse TNF receptor as defined herein. This does not of course preclude that a molecule such as a proinflammatory cytokine including its variant, derivative, truncated version or mimetic thereof might be able to bind to other receptors (i.e. a proinflammatory cytokine that is to be used to treat a human may well be able to bind to rat or mouse TNF receptors), but what is important is that the molecule such as the proinflammatory cytokine or variant, derivative, truncated version or mimetic thereof has the ability to bind to the relevant TNF receptors of the species that is to be treated.

As such, preferred molecules such as proinflammatory cytokines bind to the TNF receptor TNFR-1 and/or TNFR-2, preferably TNFR-1, of the species which are set forth elsewhere herein as being preferred species for treatment or detection of tumours in accordance with the present invention.

It can be determined readily whether a molecule binds to a particular receptor either by using functional assays which measure the biological effects or output of cytokine-receptor binding studies. For example most cytokine receptors contain a single hydrophobic transmembrane domain, a cytoplasmic kinase domain and an extra-cellular domain containing a ligand-binding region. Scintillation Proximity Assay (SPA) provides a simple, rapid method for high-throughput screening (HTS) of such ligand-binding events.

Alternatively, cytokine-receptor binding can be measuring directly e.g. using binding assays (e.g. BIAcore biosensor technology). BIAcore is a highly sensitive, label-free, approach to study binding interactions quantitatively, under controlled conditions. The technology relies on the phenomenon of "surface plasmon resonance", small changes in the reflection of monochromatic light from a metallic chip that occur when the chip's surface binds a protein or other molecule. As the nature of the bound molecule and the receptor for that molecule that has been attached to the metallic surface are not critical, such technology can easily be used to demonstrate TNFR binding. The receptors are commercially available.

Preferably the molecule such as the proinflammatory cytokine binds to the relevant TNF receptor with an affinity (Kd) of 1 pM-1 mM, e.g. 10 pM-100 μM, 100 pM-10 μM, 10 nM-100 nm, as measured by the above assays. Particularly preferred affinities are 1-1000 pM, e.g. 5-750 pM, 10-500 pM, 20-400 pM, 25-300 pM, 30-250 pM, 40-200 pM, 50-100 pM.

The biological effect of receptor binding can also be measured using appropriate reporter cells (for example NFkB reporter cells in which a reporter gene is placed under the control of a NFkB response element and the effect of receptor binding is detected by detecting expression of the reporter gene).

Examples of particularly preferred proinflammatory cytokines are TNF and lymphotoxin α.

As mentioned above, TNF was formerly known as TNFα. The molecule was also formerly known as cachectin, and TNFα-1a. As such these terms may be used interchangeably. This molecule is primarily produced in vivo as a type II transmembrane protein arranged in stable homotrimers. The transmembrane homotrimers are subjected to proteolytic cleavage to cause the release of the homotrimeric cytokine. TNF is thus active as a homotrimer. The sequence of human TNF is known and is shown below (SEQ ID NO:1).

```
  1 mstesmirdv elaeealpkk tggpqgsrrc lflslfsfli vagattlfcl lhfgvigpqr 61 eefprdlsli splaqavrss srtpsdkpva hvvanpqaeg qlqwlnrran allangvelr 121 dnqlvvpseg lyliysqvlf kgqgcpsthv llthtisria vsyqtkvnll saikspcqre 181 tpegaeakpw yepiylggvf qlekgdrlsa einrpdyldf aesgqvyfgi ial
```

TNF which is used in accordance with the invention is preferably human TNF, i.e. an active molecule made up of a trimer of three molecules having the sequence as set out above.

TNF is available commercially in the form of tasonermin, a non-glycosylated trimer of TNF peptides, produced in *E. coli*. Tasonermin thus represents a preferred form of TNF.

Lymphotoxin α which is used in accordance with the invention is a lymphokine produced by activated T lymphocytes that inhibits growth of tumours and blocks transformation of cells. It is a member of the TNF family and like TNF is active as a homotrimer.

The sequence of the human lymphotoxin α is known and is shown below (SEQ ID NO:2).

```
  1 mtpperlflp rvcgttlhll llglllvllp gaqglpgvgl tpsaaqtarq hpkmhlahst 61 lkpaahligd pskqnsllwr antdraflqd gfslsnnsll vptsgiyfvy sqvvfsgkay 121 spkatssply lahevqlfss qypfhvplls sqkmvypglq epwlhsmyhg aafqltqgdq 181 lsthtdgiph lvlspstvff gafal
```

Lymphotoxin is thus preferably human lymphotoxin i.e. an active molecule made up of a trimer of three molecules having the sequence as set out above.

Both membrane bound and soluble versions of proinflammatory cytokines as discussed herein may be used.

Variants, derivatives, truncated versions and mimetics of known proinflammatory cytokines are encompassed by reference to proinflammatory cytokines and may also be used in methods of the invention.

Any variants, derivatives, truncated versions or mimetics of proinflammatory cytokines must retain the ability of the proinflammatory cytokines to increase the permeability of tumour vasculature when systemically administered to a patient in order to be useful in the methods of the invention, however, the variants, derivatives, truncated versions or mimetics of parent proinflammatory cytokines may not necessarily retain all of the properties of the parent proinflammatory cytokines to be useful in the invention. Thus reference to "proinflammatory cytokine" does not require that the molecule retains its proinflammatory properties, but rather that it is derived from such a molecule. As discussed elsewhere herein it is straightforward to determine whether a molecule has the ability to increase the permeability of tumour vasculature when systemically administered to a patient.

Variants, derivatives and truncated versions of the proinflammatory cytokines may be proteins, polypeptides, or glycoproteins.

"Proteins" as referred to herein are molecules made up of amino acid residues linked together. "Glycoproteins" are proteins or polypeptides to which sugar groups are attached. "Peptides" preferably have fewer than 50, 40, 30 or 20 amino acids, e.g. from 5 to 50 or 10 to 20 amino acids. "Polypeptides" as referred to herein are molecules with preferably more than 50, 100, 150, 200 or 250 amino acid residues and/or less than 500, 400, 300, 200 or 100 amino acid residues or a range selected therefrom.

Variants of the proinflammatory cytokines referred to above are also of use in the invention. Such molecules may be polypeptides, proteins or glycoproteins in which case they will preferably have an amino acid sequence that is at least 55, 60, 65, 70, 75, 80, 85, 90, 95, 96, 97, 98 or 99% identical to the sequence of the relevant proinflammatory cytokine, and to which it is compared.

Sequence identity may be determined by, e.g. using the SWISS-PROT protein sequence databank using FASTA pep-cmp with a variable pamfactor, and gap creation penalty set at 12.0 and gap extension penalty set at 4.0, and a window of 2 amino acids. Preferably said comparison is made over the full length of the sequence, but may be made over a smaller window of comparison, e.g. less than 200, 100 or 50 contiguous amino acids.

To be of use in the invention such variants are functionally equivalent to the relevant proinflammatory cytokines, e.g. to those whose sequences are set forth in the recited Sequence Nos. Similarly, the polypeptides e.g. with sequences as set forth in the Sequence Nos. may be modified without affecting the sequence of the polypeptide as described below.

As referred to herein, to achieve "functional equivalence" the polypeptide, protein or glycoprotein may show some reduced efficacy in performing the function relative to the parent molecule (i.e. the molecule from which it was derived, e.g. by amino acid substitution), but preferably is as efficient or is more efficient. Thus, functional equivalence relates to a polypeptide which is effective to act as described herein, i.e. permeabilise the tumour vasculature, or to bind to a receptor as referred to above. This may be tested by comparison of the effects of the variant polypeptide, protein or glycoprotein relative to the polypeptide, protein or glycoprotein from which it is derived in a qualitative or quantitative manner, e.g. by performing the in vivo analyses referred to in the Examples. Where quantitative results are possible, the variant is at least 30, 50, 70, 80% or 90% as effective as the parent polypeptide. Alternatively, in vitro testing may be performed, e.g. by analysis of binding to a receptor as referred to above.

Functionally-equivalent polypeptides, proteins or glycoproteins which are related to or derived from the naturally-occurring polypeptides, proteins or glycoproteins, may be obtained by modifying the native amino acid sequence by single or multiple amino acid substitution, addition and/or deletion (providing they satisfy the above-mentioned sequence identity requirements), but without destroying the molecule's function. Preferably the native sequence has less than 50, 40, 30, 20 substitutions, additions or deletions, e.g.

less than 10, 5, 4, 3, 2, or 1 such modifications. Such proteins are encoded by "functionally-equivalent nucleic acid molecules" which are generated by appropriate substitution, addition and/or deletion of one or more bases.

Functional equivalents may be "addition" variants in which amino and/or carboxy terminal fusion polypeptide, protein or glycoprotein are generated, comprising an additional protein or polypeptide fused to the parent polypeptide, protein or glycoprotein. They may also be "deletion" variants, in which e.g. 1 to 50, e.g. 1 to 10, 20, 30 or 40, or 5 to 40, e.g. 10 to 35 amino acids are deleted from the N or C terminus or internally, thereby generating a truncated version of the parent polypeptide. As referred to herein such deletion variants preferably comprise at least 30, 40, 50, 60, 70, 80, 90, 100, 150, 200 or more amino acids of the sequence from which it is derived. These amino acids may be obtained from a central or N-terminal or C-terminal portions of the parent sequence. Such deletion variants are also referred to herein as truncated versions or portions of the proinflammatory cytokines.

Particularly preferred functionally-equivalent variants are natural biological variations (e.g. allelic variants or geographical variations within a species or alternatively in different genera, e.g. plants, animals or bacteria) and derivatives prepared using known techniques.

Further preferred functionally-equivalent variants include those which are modified without affecting the sequence of the polypeptide, e.g. by chemical modification, including by deglycosylation or glycosylation. Such polypeptides may be prepared by post-synthesis/isolation modification of the polypeptide without affecting functionality, e.g. certain glycosylation, methylation etc. of particular residues.

The tumour vasculature permeabilising molecules of the invention may also take the form of peptidomimetics of the proinflammatory cytokines discussed above, and which may be considered derivatives in which the functional features of the proinflammatory cytokine are retained but are presented in the context of a different, e.g. non-peptide structure. Such peptidomimetics have successfully been developed and used for other particularly medical applications.

Peptidomimetics, particularly non-peptidic molecules may be generated through various processes, including conformational-based drug design, screening, focused library design and classical medicinal chemistry. Not only may oligomers of unnatural amino acids or other organic building blocks be used, but also carbohydrates, heterocyclic or macrocyclic compounds or any organic molecule that comprises structural elements and conformation that provides a molecular electrostatic surface that mimics the same properties of the 3-dimensional conformation of the peptide may be used by methods known in the art.

Thus the peptidomimetics may bear little or no resemblance to a peptide backbone. Peptidomimetics may comprise an entirely synthetic non-peptide form (e.g. based on a carbohydrate backbone with appropriate substituents) or may retain one or more elements of the peptide on which it is based, e.g. by derivatizing one or more amino acids or replacing one or more amino acids with alternative non-peptide components. Peptide-like templates include pseudo-peptides and cyclic peptides. Structural elements considered redundant for the function of the peptide may be minimized to retain a scaffold function only or removed where appropriate. When peptidomimetics retain one or more peptide elements, i.e. more than one amino acid, such amino acids may be replaced with a non-standard or structural analogue thereof. Amino acids retained in the sequences may also be derivatised or modified (e.g. labelled, glycosylated or methylated) as long as the functional properties of the polypeptides for use in the invention are retained. The peptidomimetics are referred to as being "derivable from" a certain protein or polypeptide sequence. By this it is meant that the peptidomimetic is designed with reference to a defined protein or polypeptide sequence, such that it retains the structural features of the protein or peptide which are essential for its function. This may be the particular side chains of the protein or polypeptide, or hydrogen bonding potential of the structure. Such features may be provided by non-peptide components or one or more of the amino acid residues or the bonds linking said amino acid residues of the polypeptide may be modified so as to improve certain functions of the polypeptide such as stability or protease resistance, while retaining the structural features of the polypeptide which are essential for its function.

Examples of non-standard or structural analogue amino acids which may be used are D amino acids, amide isosteres (such as N-methyl amide, retro-inverse amide, thioamide, thioester, phosphonate, ketomethylene, hydroxymethylene, fluorovinyl, (E)-vinyl, methyleneamino, methylenethio or alkane), L-N methylamino acids, D-α methylamino acids, D-N-methylamino acids. Examples of non-conventional amino acids are listed in Table 1.

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisoleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |

-continued

| Non-conventional amino acid | Code | Non-conventional amino acid | Code |
|---|---|---|---|
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylasparatate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylorinithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylasparate | Masp | L-αmethyl-t-butylglycine | Mtbug |
| L-α-methylcysteine | Mcys | L-methylethylglycine | Metg |
| L-αmethylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenylethylamino)cyclopropane | Nmbc | L-O-methyl serine | Omser |
| | | L-O-methyl homoserine | Omhser |

Non-standard amino acids which may be used include conformationally restricted analogs, e.g. such as Tic (to replace F), Aib (to replace A) or pipecolic acid (to replace Pro).

Derivatives of the proinflammatory cytokines may be used. This includes derivatives which have been modified, e.g. to facilitate their use in pharmaceutical applications (discussed below), e.g. by the addition of targeting or functional groups, e.g. to improve lipophilicity, aid cellular transport, solubility and/or stability. Thus oligosaccharides, fatty acids, fatty alcohols, amino acids, peptides or polypeptides may be conjugated to the aforementioned proteins, polypeptides or glycoproteins.

Derivatives may also be in the form of "pro-drugs" or "pro-peptides" such that the added component may be removed by cleavage once administered, e.g. by cleavage of a substituent added through esterification and which may be removed by the action of esterases. Such pro-drugs include native precursors of the naturally occurring proteins polypeptides or glycoproteins which are cleaved e.g. by proteolysis to yield an active molecule. Such precursors may be inactive in the precursor form but may be activated by proteolytic cleavage. Modified polypeptides as described above may be tested to ensure that they retain functional activity relative to the unmodified molecule by determining if they have the same or similar medical effects.

The term "mimetics" as used herein refers to molecules that mimic the action of the relevant proinflammatory cytokine of which they are a mimetic. As discussed above, mimetics need not have all the activities of a proinflammatory cytokine of which they are a mimetic but they preferably retain the ability to bind to TNFR1 or TNFR2 as defined above. As such it can be seen that antibodies that are directed to or that bind to TNFR1 and/or TNFR2 as defined above can be mimetics and hence of use in the present invention.

Thus mimetics that bind to TNFR1 and/or TNFR2 can be antibodies directed to or that bind to TNFR1 and/or TNFR2 as defined above. Any such antibodies are preferably specific for TNFR1 and/or TNFR2 as defined above in that they bind to TNFR1 and/or TNFR2 as defined above with high affinity and in preference to other molecules.

The antibody may be monoclonal or polyclonal and the term antibody extends also to antigen-binding fragments (e.g. $F(ab)_2$, Fab and Fv fragments i.e. fragments of the "variable" region of the antibody, which comprises the antigen binding site) directed specifically to TNFR1 and/or TNFR2 as defined above.

Antibodies that bind to TNFR1 and/or TNFR2 as defined above are available commercially, e.g. the MR1-2 clone which binds to TNFR1 and the Sigma 1815 clone 22221.311 antibody which binds to TNFR2. Antibodies that bind to TNFR1 and/or TNFR2 are also described in Liqin Ban et al (PNAS 2008 105:13644-13649) as agonist antibodies.

Thus in a preferred aspect, a tumour vasculature permeabilising molecule for use in the methods, uses or compositions of the invention comprises (i) a sequence as set forth in SEQ ID NO:1 or 2, (ii) a sequence with at least 80% identity to said sequence in (i), (iii) a portion of a sequence in (i) or (ii), or (iv) an antibody which binds to TNFR1 and/or TNFR2.

The polypeptides used in compositions and uses of the invention as described elsewhere herein may be obtained or derived from naturally occurring sources or may be generated entirely or partially synthetically.

As discussed above, the tumour vasculature permeabilising molecule exerts its effect on the tumour vasculature when administered systemically to a patient. As such, to achieve the desired effect in accordance with the invention the tumour vasculature permeabilising molecule is formulated for systemic administration to said patient.

"Systemic administration" refers to administration of a drug or compound to a patient such that it becomes widely distributed in the body in significant amounts and has a biological effect, in the blood. Alternatively stated, the drug or compound reaches its desired site of action via the vascular system. In the present case systemic administration includes any administration which is not directly to the tumour (e.g. intratumoural).

Typical systemic routes of administration include administration by introducing the agent directly into the vascular system (e.g. intravenously (into a vein), intraarterially (into an artery) or intraosseous infusion (into the bone marrow)). These are examples of parenteral routes of administration.

Enteral routes of administration (where the relevant substance is given via the digestive tract) include a pulmonary route, or intramuscular administration wherein the agent is adsorbed, enters the vascular system, and is carried to one or more desired site(s) of action via the blood. Enteral administration may be by mouth (orally), in which case the compound may be adminstered in the form of a tablet, capsule, or liquid formulation. Alternative enteral routes of administration are by a feeding tube e.g. a gastric, duodenal or gastrostomy feeding tube, or rectal administration (e.g. in suppository or enema form).

To achieve systemic administration, the compositions of the invention may be formulated in a conventional manner with one or more physiologically acceptable carriers, excipients and/or diluents, according to techniques well known in the art using readily available ingredients.

Preferably the tumour vasculature permeabilising molecule is formulated for intravenous administration to said patient.

Thus, the tumour vasculature permeabilising molecule may be incorporated (optionally together with other active substances as a combined preparation), with one or more conventional carriers, diluents and/or excipients, to produce conventional galenic preparations such as tablets, pills, powders, lozenges, sachets, cachets, elixirs, suspensions (as injection or infusion fluids), emulsions, solutions, syrups, aerosols (as a solid or in a liquid medium), ointments, soft and hard gelatin capsules, suppositories, sterile injectable solutions, sterile packaged powders, and the like. Biodegradable polymers (such as polyesters, polyanhydrides, polylactic acid, or polyglycolic acid) may also be used for solid implants. The compositions may be stabilized by use of freeze-drying, undercooling or Permazyme.

Suitable excipients, carriers or diluents are lactose, dextrose, sucrose, sorbitol, mannitol, starches, gum acacia, calcium phosphate, calcium carbonate, calcium lactose, corn starch, aglinates, tragacanth, gelatin, calcium silicate, microcrystalline cellulose, polyvinylpyrrolidone, cellulose, water syrup, water, water/ethanol, water/glycol, water/polyethylene, glycol, propylene glycol, methyl cellulose, methylhydroxybenzoates, propyl hydroxybenzoates, talc, magnesium stearate, mineral oil or fatty substances such as hard fat or suitable mixtures thereof. Agents for obtaining sustained release formulations, such as carboxypolymethylene, carboxymethyl cellulose, cellulose acetate phthalate, or polyvinylacetate may also be used.

The compositions may additionally include lubricating agents, wetting agents, emulsifying agents, viscosity increasing agents, granulating agents, disintegrating agents, binding agents, osmotic active agents, suspending agents, preserving agents, sweetening agents, flavouring agents, adsorption enhancers (e.g. surface penetrating agents or for nasal delivery, e.g. bile salts, lecithins, surfactants, fatty acids, chelators), browning agents, organic solvent, antioxidant, stabilizing agents, emollients, silicone, alpha-hydroxy acid, demulcent, anti-foaming agent, moisturizing agent, vitamin, fragrance, ionic or non-ionic thickeners, surfactants, filler, ionic or non-ionic thickener, sequestrant, polymer, propellant, alkalinizing or acidifying agent, opacifier, colouring agents and fatty compounds and the like.

The compositions of the invention may be formulated so as to provide quick, sustained or delayed release of the active ingredient after administration to the body by employing techniques well known in the art.

The composition may be in any appropriate dosage form to allow delivery or for targetting particular cells or tissues, e.g. as an emulsion or in liposomes, niosomes, microspheres, nanoparticles or the like with which the active ingredient may be absorbed, adsorbed, incorporated or bound. This can effectively convert the product to an insoluble form. These particulate forms may overcome both stability (e.g. degradation) and delivery problems. These particles may carry appropriate surface molecules to improve circulation time (e.g. serum components, surfactants, polyoxamine-908, PEG etc.) or moieties for site-specific targeting, such as ligands to particular cell borne receptors. Appropriate techniques for drug delivery and for targeting are well known in the art and are described in WO99/62315.

The use of solutions, suspensions, gels and emulsions are preferred, e.g. the active ingredient may be carried in water, a gas, a water-based liquid, an oil, a gel, an emulsion, an oil-in water or water-in-oil emulsion, a dispersion or a mixture thereof.

Forms adapted for oral or parenteral administration include plain or coated tablets, capsules, suspensions and solutions containing the active component optionally together with one or more inert conventional carriers and/or diluents, e.g. with corn starch, lactose, sucrose, microcrystalline cellulose, magnesium stearate, polyvinylpyrrolidone, citric acid, tartaric acid, water, water/ethanol, water/glycerol, water/sorbitol, water/polyethylene glycol, propylene glycol, stearyl alcohol, carboxymethylcellulose or fatty substances such as hard fat or suitable mixtures thereof.

Said tumour vasculature permeabilising molecule is thus preferably formulated for systemic administration to said patient by a parenteral or enteral route, and is particularly preferably formulated for systemic administration to said patient by intravenous administration.

In a particularly preferred embodiment, the tumour vasculature permeabilising molecule is preferably formulated for systemic administration such that a carrier protein such as albumin is also present. Such carrier proteins are widely used to stabilise active ingredients in pharmaceutical compositions and are well known in the art.

As discussed above, permeabilisation of tumour vasculature, which is achieved by systemic administration of a tumour vasculature permeabilising molecule as defined hereinbefore, allows for improved access of agents such as signal generating (e.g. imaging) agents and anticancer agents to tumours. This in turn allows the agents to exert their effects in or on the tumour in a more effective manner.

By "tumour" it is meant an abnormal mass of tissue formed by the growth of cells. For this reason they are often termed solid tumours. Tumours may also be called neoplasms and can be benign or malignant (cancerous). Benign tumours do not invade other tissues and do not form metastases. Malignant tumours on the other hand will tend to undergo invasion and metastasis, thus forming secondary tumours at distinct sites. Tumours may also be described as "pre-malignancy", "pre-cancer or "non-invasive" tumours. These are not invasive or metastatic tumours but they have the potential to progress to become invasive if they are left untreated.

A primary tumour is a tumour that is at the original site where it first arose. For example, a primary brain tumour is one that arose in the brain as opposed to one that arose elsewhere and metastasized (spread) to the brain. Secondary or metastatic tumours (metastases) on the other hand develop as a result of metastasis from the original cancer and are derived from the metastasis of a primary tumour. All such tumours may be detected, diagnosed or treated according to the methods of the present invention.

The methods of the invention may be used to detect (e.g. image) and treat any solid tumour in the periphery or in the CNS (including the brain and spinal cord). By periphery it is meant a non-CNS regions of the body.

Appropriate tumours for treatment include those present or arising in the following conditions, Adrenocortical Carcinoma, AIDS-Related Cancers, Anal Cancer, Appendix Cancer, Astrocytoma, Bladder Cancer, Bone Cancer (Osteosarcoma and Malignant Fibrous Histiocytoma), Brain Tumor, Breast Cancer, Burkitt Lymphoma, Gastrointestinal Carcinoid Tumor, Carcinoma of Unknown Primary, Primary Central Nervous System Lymphoma, Cervical Cancer, Colon Cancer, Endometrial Cancer, Esophageal Cancer, Ewing Family of Tumors, Extragonadal Germ Cell Tumor, Extrahepatic Bile Duct Cancer, Eye Cancer (Intraocular Melanoma or Retinoblastoma), Gallbladder Cancer, Gastric (Stomach) Cancer, Gastrointestinal Carcinoid Tumor, Gastrointestinal Stromal Tumor (GIST) Germ Cell Tumor (Extragonadal), Germ Cell Tumor, (Ovarian) Gestational Trophoblastic Tumor, Glioma, Hairy Cell Leukemia, Head and Neck Cancer, Hepatocellular (Liver) Cancer, (Primary), Hodgkin Lymphoma, Hypopharyngeal Cancer, Intraocular Melanoma, Islet Cell Tumors (Endocrine Pancreas), Kaposi Sarcoma, Kidney (Renal Cell) Cancer, Laryngeal Cancer, Leukemia (Acute Lymphoblastic, Acute Myeloid, Chronic Lymphocytic, Chronic Myelogenous, Hairy Cell), Lip and Oral Cavity Cancer, Liver Cancer, Lung Cancer, (Non-Small Cell or Small Cell), Primary Central Nervous System Lymphoma, Macroglobulinemia, Waldenström, Malignant Fibrous Histiocytoma of Bone and Osteosarcoma, Melanoma (including Intraocular (Eye) Melanoma), Merkel Cell Carcinoma, Mesothelioma, Metastatic Squamous Neck Cancer with Occult Primary, Mouth Cancer, Multiple Myeloma/Plasma Cell Neoplasm, Mycosis Fungoides, Myelodysplastic Syndromes, Myelodysplastic/Myeloproliferative Diseases, Multiple Myeloma, Chronic Myeloproliferative Disorders, Nasal Cavity and Paranasal Sinus Cancer, Nasopharyngeal Cancer, Neuroblastoma, Non-Hodgkin Lymphoma, Lip and Oral Cavity Cancer, Oropharyngeal Cancer, Osteosarcoma and Malignant Fibrous Histiocytoma of Bone, Ovarian (Epithelial or Germ cell) Cancer, Pancreatic Cancer (including Islet Cell Tumors), Paranasal Sinus and Nasal Cavity Cancer, Parathyroid Cancer, Penile Cancer, Pharyngeal Cancer, Pheochromocytoma, Pituitary Tumor, Plasma Cell Neoplasm/Multiple Myeloma, Pleuropulmonary Blastoma, Primary Central Nervous System Lymphoma, Prostate Cancer, Rectal Cancer, Renal Cell (Kidney) Cancer, Renal Pelvis and Ureter Transitional Cell Cancer, Respiratory Tract Carcinoma Involving the NUT Gene on Chromosome 15, Retinoblastoma, Salivary Gland Cancer, Sarcoma, Soft Tissue Sarcoma, Uterine Sarcoma, Sézary Syndrome, Skin Cancer (Nonmelanoma, Melanoma, Merkel Cell), Skin Carcinoma, Small Intestine Cancer, Squamous Neck Cancer with Occult Primary (Metastatic), Stomach (Gastric) Cancer, Testicular Cancer, Throat Cancer, Thymoma and Thymic Carcinoma, Thyroid Cancer, Carcinoma of Unknown Primary Site, Urethral Cancer, Uterine Cancer (Endometrial), Vaginal Cancer, Vulvar Cancer, Waldenström Macroglobulinemia and Wilms Tumor.

Preferred peripheral tumours include visceral tumours, i.e. tumours that are present in an internal organ of the thorax or abdomen, e.g. a liver tumour (such as a liver tumour that has metastasised e.g. from a colorectal cancer, breast cancer or lung cancer). Further preferred peripheral tumours include rectal tumours (e.g. rectal tumours with local invasion), small bowel carcinoid tumours, pancreatic tumours and renal cell carcinoma, lung, bone and breast tumours.

Furthermore, when the methods as described herein are used to treat or detect tumours in the periphery, such tumours are preferably metastatic. The tumours are also preferably small. The amount of tumour vasculature permeabilising agent to be used for the treatment or detection of peripheral tumours is also preferably as set out as preferred elsewhere herein. Preferably human peripheral tumours are treated or detected.

The methods of the invention are, however, preferably used to detect (e.g. image) and treat tumours that are found beyond or behind the BBB, i.e. CNS, including brain tumours. Within the CNS intraaxial tumours or tumours occurring in intraaxial structures are preferred. Examples of CNS tumours include Gliomas (e.g. astrocytoma, ependymoma, oligodendroglioma and mixed glioma), Acoustic neuromas, Astrocytomas (including glioblastoma multiforme), Craniopharyngiomas, Ependymomas, Haemangioblastomas, Meningiomas, Pineal region tumours, Pituitary tumours (e.g. adenomas), Primitive neuroectodermal tumours (PNETs) and Spinal cord tumours.

The methods of the invention are also preferably used to detect (e.g. image) and treat metastases, i.e. secondary tumours, particularly when they are at an early stage and hence are small. Small tumours are of a size as defined elsewhere herein. Metastases (preferably small metastases) in the CNS form a particularly preferred subgroup for detection and treatment.

The invention thus further provides a method of treating a tumour in a patient comprising administering to said patient a tumour vasculature permeabilising molecule and an anticancer agent, wherein said tumour vasculature permeabilising molecule is systemically administered to said patient.

Alternatively stated the invention provides a tumour vasculature permeabilising molecule and an anticancer agent for use in treating a tumour in a patient, wherein said tumour vasculature permeabilising molecule is formulated for (and intended for) systemic administration to said patient.

In an alternative embodiment, the use of a tumour vasculature permeabilising molecule and an anticancer agent in the manufacture of a medicament for treating a tumour in a patient, wherein said tumour vasculature permeabilising molecule is formulated for systemic administration to said patient, is provided.

The use of a tumour vasculature permeabilising molecule in the manufacture of a medicament for treating a tumour in a patient, wherein said medicament is formulated for systemic administration to said patient, and said medicament is intended for use in combination with an anticancer agent is further provided, as is the use of an anticancer agent in the manufacture of a medicament for treating a tumour in a patient, wherein said medicament is intended for use in combination with a tumour vasculature permeabilising molecule which is formulated for systemic administration to said patient.

In all cases, said tumour vasculature permeabilising molecule is intended for systemic administration. Further preferably said anticancer agent is also formulated for systemic administration to said patient. Even more preferably said anticancer agent is also intended for systemic administration. Modes of systemic administration and appropriate formulations are discussed above.

In all cases said tumour is preferably a CNS, including brain tumour, or a metastasis (preferably a small metastasis). Metastatic tumours (preferably small metastatic tumours) in the CNS form a particularly preferred subgroup for detection and treatment.

As used herein, "treating" refers to the reduction, alleviation or elimination, preferably to normal levels, of one or more of the symptoms or effects of said tumour relative to the symptoms or effects present in a corresponding tumour not subject to said treatment. Treatment or treating refers to both therapeutic treatment and prophylactic or preventative measures, wherein the object is to prevent or slow down (lessen) the growth or progression of the tumour. Insofar as prevention or prophylaxis are concerned, these result directly from the "treatment" of the tumour. For example if a tumour is successfully treated, it may not go on to metastasise and spread to another region of the patient. As such metastatic spread is prevented, but it is the tumour itself which is treated.

As a result of the treatment of a tumour the overall size of the tumour, the number of cells in the tumour, or the number of viable cells in the tumour may increase more slowly (i.e. the tumour may continue to grow, but to do so at a reduced rate), may not increase or may decrease. Alternatively stated, the metastatic or invasive potential or the size of the tumour may increase more slowly (i.e. may continue to become metastatic but is doing so at a reduced rate), may not increase (in that the tumour does not become metastatic or invasive) or may decrease.

The rate of tumour growth or the rate at which the tumour becomes metastatic or invasive may be less than 0.9, 0.8, 0.7, 0.6, 0.5, 0.4, 0.3, 0.2, 0.1 fold that of a corresponding tumour not subject to said treatment.

Any decrease in size of the tumour may be by at least about 20, 30, 40, 50, 60, 70, 80, 90 or 100% by volume. Any decrease in cell number or viable cell number may be by at least about 20, 30, 40, 50, 60, 70, 80, 90 or 100%.

Tumour size, cell number (including viable cell number) and ability to metastasize may be monitored through standard techniques known in the art.

Accordingly, "treating" broadly includes maintaining a subject's disease progression or symptoms at a substantially static level, increasing a subject's rate of recovery, amelioration and/or prevention of the onset of the symptoms or severity of the condition, or extending a patient's quality of life.

By "anticancer agent" it is meant any agent that can be used to treat a tumour in accordance with the definition provided above. Anticancer agents are well known in the art and any suitable anticancer agent may be used in the present invention. The nature of the particular anticancer agent is not important; all that is required is that it exerts an effect on the tumour, once it has been permitted to access it.

Examples of suitable anticancer agents for use in connection with the present invention include chemotherapeutic agents, oncolytic viruses and exosomes containing therapeutic nucleic acid molecules.

A "chemotherapeutic agent" is a chemical compound useful in the treatment of cancer. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carnomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL®, Bristol-Myers Squibb Oncology, Princeton, N.J.) and docetaxel (TAXOTERE®, Aventis, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-I1; topoisomerase inhibitor RFS 2000; difluoromethylornithine (DMFO); retinoic acid; esperamicins; capecitabine; and pharmaceutically acceptable salts, acids or derivatives of any of the above.

Also included in this definition are anti-hormonal agents that act to regulate or inhibit hormone action on tumours such as anti-estrogens including for example tamoxifen, raloxifene, aromatase inhibiting 4(5)-imidazoles, 4-hydroxytamoxifen, trioxifene, keoxifene, LY1 17018, onapristone, and toremifene (Fareston); and anti-androgens such as flutamide, nilutamide, bicalutamide, leuprolide, and goserelin; and pharmaceutically acceptable salts, acids or derivatives of any of the above.

Also included are curcumin, lapatinib (Tykerb), tyrosine kinase inhibitors (e.g. Erlotinib (Tarceva), Imatinib (Glivec), Gefitinib (iressa), Dasatinib (Sprycel), Sunitinib and Nilotinib), proteasome inhibitors (e.g. Bortezomib (Velcade)) and monoclonal antibodies such as trastuzumab (Herceptin), Cetuximab and Panitumumab and pharmaceutically acceptable salts, acids or derivatives of any of the above.

In view of the high occurrence of secondary brain cancer from a primary breast cancer, preferred chemotherapeutic agents for treating brain cancer are those which are used to treat breast cancer.

Particularly preferred chemotherapeutic agents include lapatinib, doxorubicin, trastuzumab, melphalan, paclitaxel and these compounds or combinations thereof are preferably used in the methods of the invention.

An oncolytic virus is a virus that preferentially infects and kills cancer cells by lysing them; these have obvious functions for cancer therapy, both by direct destruction of the tumour cells, and, if modified, as vectors enabling genes expressing anticancer proteins to be delivered specifically to the tumour site. Oncolytic viruses are regulated by the tumour phenotype to replicate and lyse cancer cells selectively. Examples of adenoviruses with distinct regulatory mechanisms are: Ad-dl922-947 (targets G1-S checkpoint); Ad-Onyx-015 and Ad-Onyx-017 (target p53/mRNA export); Ad-vKH1 (targets Wnt pathway) and AdEHE2F (targets estrogen receptor/G1-S checkpoint/hypoxic signalling). (Seymour L W et al Hum Gene Ther. 2008 Jun. 27. [Epub ahead of print]).

Any suitable oncolytic virus, alone or in combination with one or more other oncolytic virus may be used as the anticancer agent in the present invention.

Exosomes containing therapeutic nucleic acid molecules (e.g. siRNA or a nucleic acid molecule or vector encoding a therapeutically active protein) can also be used as an anticancer agent. Examples of siRNA that can be included are siRNA molecules that target tyrosine kinases or the wnt signalling pathway.

A single anticancer agent or combinations of two or more thereof may be used.

The above discussion relates to the treatment of tumours, and as discussed above the systemic administration of a tumour vasculature permeabilising molecule will also improve methods of detecting tumours that rely or are enhanced by the use of a signal generating, e.g. imaging agent.

Imaging techniques to detect tumours in vivo often uses imaging agents which are administered to the patient and which serve to improve or enhance the resultant images so that any tumours are more readily detectable. Imaging methods such as X-ray, CT scans and MRI have for many years employed such imaging agents. Although images that provide useful information can be obtained in the absence of imaging agents, the use of these agents can vastly improve the images that are obtained and hence improve the information that is obtained from carrying out the imaging. For example on an MRI image taken without a contrast agent, tumours from about 1-2 centimetres in size and larger can easily be detected, however as noted above it is desirable to be able to detect smaller tumours and hence contrast-enhanced imaging is advantageous.

In order to be able to function as imaging agents, the relevant agents must enter or interact with the tumour tissue itself. As discussed above, in such cases the success of the detection method will rely on the ability of the imaging agent to access or make contact with the tumour. Since the systemic administration of a tumour vasculature permeabilising molecule to a patient will permeabilise the tumour vasculature as discussed above, this will result in imaging agents also being able to cross the tumour vasculature to access the tumour more readily than in the absence of a systemically administered tumour vasculature permeabilising molecule. It is clear from this that imaging methods which rely on the access of an imaging agent to the tumour will thus be improved relative to known imaging methods.

In a further embodiment therefore the present invention provides a method of detecting a tumour in a patient comprising administering to said patient a tumour vasculature permeabilising molecule and a signal generating (e.g. imaging) agent, wherein said tumour vasculature permeabilising molecule is systemically administered to said patient.

Alternatively stated, the invention provides a tumour vasculature-permeabilising molecule and a a signal generating (e.g. imaging) agent for use in detecting the presence or absence of tumours in a patient, wherein said tumour vasculature permeabilising molecule is formulated for (and intended for) systemic administration to said patient.

In an alternative embodiment, the use of a tumour vasculature permeabilising molecule and a signal generating (e.g. imaging) agent in the manufacture of a diagnostic reagent for detecting the presence or absence of a tumour in a patient, wherein said tumour vasculature permeabilising molecule is formulated for (and intended for) systemic administration to said patient is further provided.

The use of a tumour vasculature permeabilising molecule in the manufacture of a diagnostic reagent for detecting the presence or absence of a tumour in a patient, wherein said diagnostic reagent is formulated for systemic administration to said patient, and said diagnostic reagent is intended for use in combination with a signal generating (e.g. imaging) agent is furthermore provided as is the use of a signal generating (e.g. imaging) agent in the manufacture of a diagnostic reagent for detecting the presence or absence of a tumour in a patient, wherein said diagnostic reagent is intended for use in combination with a tumour vasculature permeabilising molecule which is formulated for (and intended for) systemic administration to said patient.

In all cases, said tumour vasculature permeabilising molecule is intended for systemic administration to said patient. Further preferably said signal generating (e.g. imaging) agent is also formulated for systemic administration to said patient. Even more preferably said signal generating (e.g. imaging) agent is also intended for systemic administration.

In all cases, the further step of recording the signal (e.g. obtaining an image) of the patient can then be carried out to detect the presence or absence of said tumour, and forms a further optional step in the above methods and uses.

The image thus recorded or obtained can be analysed in order to determine whether it is indicative of the presence of a tumour and thereby it can be determined whether a tumour is present or absent.

By "detecting the presence or absence of a tumour" it is meant carrying out steps to determine whether or not a tumour can be observed e.g. using imaging techniques such as MRI. The image of the patient that is obtained by carrying out the imaging technique is thus observed and it is determined whether the resultant image is indicative of the presence of a tumour, or whether it is indicative of the absence of a tumour (or the absence of a tumour that is of such a size as can be detected by that particular technique). It is expected that very small tumours (e.g. less than 0.1 mm in diameter) will not be detectable and as such a conclusion that there is no tumour is in fact a conclusion that no tumour of a detectable size is present.

This can be performed by reference to appropriate controls and/or references, such as patients who are known not to have a tumour, or to other regions of the patient's body which do not have a tumour.

As discussed above, systemic administration of the tumour vasculature permeabilising molecule causes tumour vasculature to become permeabilised. The signal generating e.g. imaging agent can then access the tumour. Once the patient has been administered with both the tumour vasculature permeabilising molecule and the signal generating e.g. imaging, agent the step of detecting that agent, e.g. of recording an image of the patient can then occur.

This can be done for example by X-ray, CT scan or magnetic resonance imaging (MRI).

The above described methods are particularly advantageous for detecting the presence or absence (and also of treating) of small tumours. Small tumours are tumours that are less than 20 mm, 15 mm, 10 mm, 5 mm, e.g less than 4, 3, 2, 1, 0.5, 0.25 mm in diameter. As mentioned above, tumours less than 0.1 mm in diameter may not be detectable and as such the methods are preferably of use for detecting the presence or absence or for treating tumours that are 0.1-20, 0.25-15, 0.5-10, 1-5 or 2-4 mm in diameter.

As discussed in more detail above, the existence of the BBB is such that small tumours that are behind or beyond the BBB are particularly difficult to detect. As such the methods described herein are of particular application to tumours that are behind or beyond the BBB, including the list of tumours referred to above. Metastases (preferably small metastases) in the CNS form a particularly preferred subgroup for detection and treatment.

The above described methods are also particularly advantageous for detecting metastatic tumours particularly when they are at an early stage, i.e. when they are small, i.e. of the sizes referred to above. Whilst the methods can be used to detect metastases throughout the body, this is particularly true when said tumour is behind or beyond the BBB.

When the methods as described herein are used to detect tumours in the periphery, such tumours are preferably metastatic and preferably small. When the methods as described herein are used to detect tumours in the periphery the amount of tumour vasculature permeabilising agent used is also preferably as set out as preferred elsewhere herein. When the methods as described herein are used to detect tumours in the periphery, this is preferably in a human.

A "signal generating agent" as referred to herein is an agent, wherein by virtue of its association with the tumour, provides a detectable signal, or enhances an existing signal (e.g. radiation, light) and the increased signal (relative to normal) can be used to establish the presence or absence of a tumour. Preferably the signal generating agent is an imaging agent.

The "imaging" agent is any agent which is used to obtain or to produce or to enhance an image of a patient, and particularly any agent which is used to obtain or to produce or to enhance an image of a tumour in a patient.

The imaging agent may be an agent which enters or interacts with tumour tissue. Such agents may or may not also interact normal or non-tumour tissue, but in general they will preferentially interact with or bind to tumour tissue. Examples of such imaging agents are labelled antibodies and passive contrast agents and targeted contrast agents. Such agents are often termed "blood pool contrast agents".

Contrast agents are well known and are widely used in imaging techniques to increase the signal difference between the area of interest and background and include gadolinium-based compounds and iron oxide contrast agents (Superparamagnetic Iron Oxide (SPIO) and Ultrasmall Superparamagnetic Iron Oxide (USPIO)).

Examples of appropriate imaging agents include X-ray contrast agents such as Acetrizoic Acid Derivatives, Diatrizoic Acid Derivatives, Iothalamic Acid Derivatives, Ioxithalamic Acid Derivatives, Metrizoic Acid Derivatives, Iodamide, Lypophylic Agents, Aliphatic Acid Salts, Iodipamide, Ioglycamic Acid, Ioxaglic Acid Derivatives, Metrizamide, Iopamidol, Iohexyl, Iopromide, Iobitridol, Iomeprol, Iopentol, Ioversol, Ioxilan, Iodixanol, Iotrolan, MRI contrast agents such as gadopentetate dimeglumine, gadoteridol, gadoterate meglumine, mangafodipir trisodium, gadodiamide, Gadopentetic acid, Gadoteric acid, Gadolinium, Mangafodipir, Gadoversetamide, Ferric ammonium citrate, Gadobenic acid, Gadobutrol, Gadoxetic acid, Superparamagnetic, Ferumoxsil, Ferristene, Iron oxide, nanoparticles, Perflubron, Ultrasound agents such as Microspheres of human albumin, Microparticles of galactose, Perflenapent, Microspheres of phospholipids and Sulphur hexafluoride. Positron Emission Tomography (PET) and Single photon emission computed tomography (SPECT) agents that are normally excluded from the brain may also be used.

Preferably the imaging is carried out in a non-invasive manner (e.g. by MRI, X-ray, SPECT, PET or CT scan).

The present invention further provides a method of diagnosing a tumour as described herein in an animal, comprising at least the steps of determining the presence or absence of said tumour, wherein the presence of a signal, e.g. an image that is indicative of a tumour, e.g. on the recorded image is diagnostic of the patient having a tumour. The tumour may be detected by, for example, imaging using the methods described hereinbefore. The animal is preferably as described herein. Diagnosis may be achieved by comparison of images obtained from the patient to images obtained from patients who are known not to have any tumours (or tumours that are very small (e.g. below limits of detection (e.g. <0.1 mm or <0.05 mm in diameter).

As such the invention provides a method of diagnosing a tumour in a patient comprising administering to said patient a tumour vasculature permeabilising molecule and a signal generating e.g. imaging, agent, wherein said tumour vasculature permeabilising molecule is systemically administered to said patient, detecting the signal from said signal generating agent (e.g. recording an image of said patient), determining the presence or absence of tumours by assessing the level of said signal (e.g. on said recorded image) and diagnosing said patient on the basis of the presence or absence of said tumours on the recorded image.

Alternatively stated the invention provides a tumour vasculature permeabilising molecule and a signal generating e.g. imaging, agent for use in diagnosing a tumour in a patient, wherein said tumour vasculature permeabilising molecule is formulated for (and intended for) systemic administration to said patient.

In an alternative embodiment, the use of a tumour vasculature permeabilising molecule and a signal generating e.g. imaging, agent in the manufacture of a reagent (e.g. a diagnostic reagent) for diagnosing a tumour in a patient, wherein said tumour vasculature permeabilising molecule is formulated for (and intended for) systemic administration to said patient, is provided.

The use of a tumour vasculature permeabilising molecule in the manufacture of a reagent (e.g. a diagnostic reagent) for diagnosing a tumour in a patient, wherein said reagent is formulated for systemic administration to said patient, and said reagent is intended for use in combination with a signal generating e.g. imaging agent is further provided, as is the use of signal generating e.g. imaging, agent in the manufacture of a medicament for diagnosing a tumour in a patient, wherein said reagent (e.g. a diagnostic reagent) is intended for use in combination with a tumour vasculature permeabilising molecule which is formulated for (and intended for) systemic administration to said patient.

In all cases, said tumour vasculature permeabilising molecule is intended for systemic administration to said patient. Further preferably said a signal generating (e.g. imaging) agent is also formulated for systemic administration to said patient. Even more preferably said a signal generating (e.g. imaging) agent is also intended for systemic administration.

In all cases described above, the patient as referred to herein is preferably a mammal, reptile, bird, insect or fish (e.g. salmon or cod). Preferably the patient is a mammal, particularly a primate, domestic animal, livestock or laboratory animal. Thus preferred patients include mice, rats, rabbits, guinea pigs, cats, dogs, monkeys, pigs, cows, goats, sheep and horses. Especially preferably the patient is a human.

The tumour vasculature permeabilising molecule may be administered in any amount which is effective to induce the permeability of the tumour vasculature as discussed elsewhere herein. Preferably the tumour vasculature permeabilising molecule is formulated such that 0.1-500 $\mu g/m^2$ tumour vasculature permeabilising molecule is administered to said patient. Even more preferably the tumour vasculature permeabilising molecule is formulated such that 0.5-450, 1-400, 1.5-350, 2-300, 2.5-250, 5-200, 10-150, 15-100, 20-75 or 25-50 $\mu g/m^2$ tumour vasculature permeabilising molecule is administered to said patient, preferably in a single dose. Thus in methods or uses of the invention said tumour vasculature permeabilising molecule is administered at, or intended for administration at a dose as indicated above. The above amounts relate to preferred doses for human TNF and for other molecules amounts that generate equivalent effects can be used, or else the above recited amounts can be used. Preferably the tumour vasculature permeabilising molecule is formulated such that an amount is used that is less than the maximal tolerated dose for the appropriate tumour vasculature permeabilising molecule is administered to said patient.

It may be possible to further reduce the dose of tumour vasculature permeabilising molecule by formulating the tumour vasculature permeabilising molecule for coadministration with a compound that ameliorates the unwanted side effects of the tumour vasculature permeabilising molecule. Such additional compounds or adjunct therapies (such as antiapoptotic agents) can be used to reduce any harmful or undesirable side effects of the tumour vasculature permeabilising molecule, thus allowing a higher dose to be administered. Thus in a preferred embodiment, the tumour vasculature permeabilising molecule is formulated for administration with a compound that ameliorates the unwanted side effects of the tumour vasculature permeabilising molecule, such as an antiapoptotic reagent.

The anticancer agent and the signal generating e.g. imaging, agent are administered in any amount which is effective to treat or to image the tumour. The concentrations or doses to be used will depend on the nature of the agent and the concentrations or doses should be determined in accordance with the manufacturer's guidelines. It is likely that lower concentrations or doses than those recommended can be used, e.g. less than 95, 90, 85, 80, 75, 70, 65, 60, 55, 50, 45, 40, 35, 30, 25, 20, 15 or 10% of the concentration or dose recommended for a particular agent can be used.

As discussed above, systemic administration of the tumour vasculature permeabilising molecule causes transient permeabilisation of the tumour vasculature. As such, the administration of the tumour vasculature permeabilising molecule and the anticancer agent or the signal generating e.g. imaging, agent as appropriate preferably occurs simultaneously or at such a time interval such that the anticancer agent or the signal generating e.g. imaging, agent is present in the vascular system during the time at which the tumour vasculature is permeabilised.

Depending on the pharmacokinetics of the relevant anticancer agent or the signal generating e.g. imaging, agent the anticancer agent or the signal generating e.g. imaging, agent may be administered prior to the tumour vasculature permeabilising molecule (e.g. up to 1, 2, 3, 4, 5, 6, 7, 8, 9, 10, 12, 14, 16, 18, 20, 22, 24 hours before the tumour vasculature permeabilising molecule), simultaneously with the tumour vasculature permeabilising molecule or subsequent to the tumour vasculature permeabilising molecule (e.g. up to 1, 2, 3, 4, 5, 6, 7, 8, 9, 10, 12, 14, 16, 18, 20, 22, 24 hours after the tumour vasculature permeabilising molecule), e.g. 1-12, 2-11, 3-10, 4-9, 5-8, 6-7 hours after the tumour vasculature permeabilising molecule.

Preferably the signal is detected around 4 hours (e.g. from 3 to 6 hours) after the administration of the signal generating agent and this detection step forms a preferable step in the methods and uses referred to above.

As discussed above, the tumour vasculature permeabilising molecule and the anticancer or signal generating e.g. imaging agent can be administered together or separately. The invention thus further provides a product comprising a tumour vasculature permeabilising molecule and an anticancer agent as a combined preparation for simultaneous, separate or sequential use in treating a tumour, wherein said tumour vasculature permeabilising molecule is formulated for systemic administration to said patient.

Also provided is a product comprising a tumour vasculature permeabilising molecule and a signal generating, e.g. imaging agent as a combined preparation for simultaneous, separate or sequential use in detecting the presence or absence of a tumour, wherein said tumour vasculature permeabilising molecule is formulated for systemic administration to said patient.

Also provided is a product comprising a tumour vasculature permeabilising molecule and a signal generating, e.g. imaging agent as a combined preparation for simultaneous, separate or sequential use in diagnosing a tumour, wherein said tumour vasculature permeabilising molecule is formulated for systemic administration to said patient.

Preferred tumour vasculature permeabilising molecules, anticancer agents and signal generating e.g. imaging, agents, doses, formulations and concentrations thereof are as set out elsewhere herein.

The invention further provides a pharmaceutical composition comprising a tumour vasculature permeabilising molecule and an anticancer agent or signal generating, e.g. imaging agent.

Any tumour vasculature permeabilising molecule as defined herein can be used in said composition, in combination with any anticancer agent or signal generating, e.g. imaging, agent as defined herein.

The composition is preferably formulated to be suitable to administer the doses of tumour vasculature permeabilising molecule referred to above as preferred doses. The composition is preferably formulated for administration in a volume of 0.2 ml-20 ml, e.g. 0.5 or 1 ml-10 ml or 1.5 ml-5 ml. As such a total dose of 1 mg tumour vasculature permeabilising molecule will equate to a total concentration of 0.5 mg/ml-5 mg/ml in a volume of 0.2 ml-20 ml and a total dose of 0.2 µg tumour vasculature permeabilising molecule will equate to a total concentration of 0.01 µg/ml-1 µg/ml in a volume of 0.2 ml-20 ml. The tumour vasculature permeabilising molecule is thus present at a total concentration of 0.01 µg/ml-5 mg/ml, e.g. 0.1 µg/ml-1 mg/ml, 0.5 µg/ml-500 µg/ml, 1 µg/ml-400 µg/ml, 2 µg/ml-300 µg/ml, 5 µg/ml-250 µg/ml, 10 µg/ml-200 µg/ml, 25 µg/ml-150 µg/ml, 50 µg/ml-100 µg/ml.

The tumour vasculature permeabilising molecule as described hereinbefore and signal generating, e.g. imaging, or anticancer agent as described hereinbefore may be present in said compositions as the sole active ingredients or may be combined with other ingredients, particularly other active ingredients, e.g. to augment the therapeutic effect or to make the composition more appealing to the consumer. Preferred anticancer agents and signal generating e.g. imaging, agents, doses, formulations and concentrations thereof are as set out elsewhere herein. Preferred compositions comprise the agents referred to above as being preferred anticancer agents or signal generating agents.

Examples of additional molecules that can be present are carrier proteins and adjuncts as defined elsewhere herein.

By "pharmaceutically acceptable" or "physiologically acceptable" is meant that the ingredient must be compatible with other ingredients in the composition as well as physiologically acceptable to the recipient.

The active ingredients for administration may be appropriately modified for use in a pharmaceutical composition. For example the compounds used in accordance with the invention may be stabilized against degradation by the use of derivatives or carrier proteins as described above.

The active ingredient may also be stabilized in the compositions for example by the use of appropriate additives such as salts or non-electrolytes, acetate, SDS, EDTA, citrate or acetate buffers, mannitol, glycine, HSA or polysorbate.

The following Examples are given by way of illustration only in which the Figures referred to are as follows:

FIG. 1

(A) Shows that accumulation of plasma proteins from the bloodstream (visualised by i.v. injection of Evans Blue dye) in EL4 tumour xenografts can be dramatically increased by i.v. injection of 1 µg of human recombinant TNF. (B) Shows the number of virus particles per mg of tissue following treatment with vehicle only, TNF, Angiotensin II [A2] and combrestatin (OXI4503). (C) Shows the percentage administered dose of virus present in liver, tumour and spleen and different TNF concentrations.

FIG. 2

Shows VCAM-1 expression following histological analysis of human brain metastasis. (A) is a positive control and shows VCAM-1 expression on a brain vessel (*) adjacent to acute inflammation. (B) shows normal brain tissue showing minimal VCAM-1 reaction in cortical vessel (*). (C) shows strong VCAM-1 expression in stromal endothelial cells of metastatic carcinoma (*). Solid carcinoma lobule in upper left corner. (D) shows membrane staining of the carcinoma cells themselves. The stromal vessel staining is also present, but weaker than that of the tumour cells (*). (E) shows strong endothelial VCAM-1 expression in a stromal vessel of a metastasis that evoked chronic inflammation (*). (F) and (G) show strong and selective expression of VCAM-1 by endothelial cells in close proximity to perivascular brain micrometastases (arrows), i.e. early brain metastasis. The long arrow in G indicates the intimate association of three tumour cells (long arrow in G) with a VCAM-1 positive small vessel. VCAM-1 reaction product appears as a brown signal in all images.

FIG. 3

Shows VCAM-1 expression in a murine model of brain cancer. In the original, cell nuclei are in blue, tumour cells in green and VCAM-1 in red; field of view is 300 µm×300 µm.

FIG. 4

Shows the sites of extravasation of horseradish peroxidase (HRP) administered intravenously following administration of 1 µg TNF. Arrows indicate the sites of extravasation of i.v. HRP at different levels throughout the brain 2 hours after the administration of 1 µg TNF.

EXAMPLES

Methods

Cell Lines and Adenoviral Preparations.

EL4 tumour xenografts were maintained in DMEM supplemented with 10% FBS and antibiotics.

All adenoviruses were grown in 293 cells, and purified by double banding in CsCl gradients with Benzonase treatment after the first banding. Viral particle (VP) number was determined by measuring DNA content, using a PicoGreen assay (Invitrogen, Carlsbad, Calif.) (Murakami and McCaman, 1999, Anal Biochem; 274(2):283-8).

Permeabilizing Tumours.

EL4 cells ($2\times10^6$) were injected subcutaneously and allowed to form tumours in the left flank of 4- to 6-week-old SCID-beige female mice. Evans Blue was administered intravenously to compare permeability in 1 µg TNFα-treated animals versus controls. Oncolytic adenovirus was injected intravascularly when tumours were 100 mm³ and relative distribution was assessed by hexon staining and quantitative polymerase chain reaction measurement of viral DNA.

Human Tissue

Surgical tissue surplus to diagnostic requirements and post-mortem tissue was retrieved from the Thomas Willis Oxford Brain Collection with approval from the local research ethics committee (reference 06/Q1604/141). Metastatic tumours were classified according to known primary site or immunohistochemical profile during routine diagnostic work-up. Well-established breast carcinoma metastases were defined as tumours that were surgically resected after a macroscopic mass lesion was identified on neuroimaging. A metastasis was included in the study if the specimen contained at least focally a well-preserved tumour-brain interface. Micrometastases were defined as tumours in the brain parenchyma that were less than 5 mm in diameter and did not contain a central solid sheet of cells. Carcinomatous metastases were those associated with carcinomatous meningitis. Micrometastases and the parenchymal component of carcinomatous growth were considered to reflect early stages of invasion.

Tumour cells were immunostained with Cam5.2 antibody (monoclonal, 1:10, BD) and endothelial cells with QBend 10 (CD34) (monoclonal, 1:200, Dako Cytomation). All immunohistochemical assays were carried out using the Dako Envision kit on routine paraffin-processed tissue. Sections were reviewed and digitally photographed with an Olympus BX51 microscope. Angiotropic invasion was defined as perivascular tumor cell growth at the tumor-brain interface. This was divided into single-cell invasion or collective (bulk) invasion (two or more cell layers thick). Angiotropic growth in cases with carcinomatous growth or micrometastases was further quantified in Cam5.2-stained sections by counting in consecutive microscopic fields the tumour cell profiles that were in a perivascular location compared to those that were not clearly vessel-associated.

Histological Analysis

Experimental tissues were collected under terminal anesthesia after transcardiac perfusion with saline and 4% paraformaldehyde or organs were freshly isolated and snap frozen or immersion fixed. After dissection, the brains were post-fixed, cryoprotected, embedded and frozen in isopentane at −40°. Immunostaining was performed on 10 µm-thick coronal brain sections using the VCAM-1 (H-276): sc-830 for human VCAM-1 (1 µg/ml) and standard ABC amplification procedures. Sections were counterstained with cresyl violet, and examined for VCAM-1 expression (stained as a brown stain). Fluorescence immunohistochemistry was performed with either standard indirect technique (fluorophore-conjugated secondary antibodies; Invitrogen) or with tyramide signal amplification (TSA). TSA kits from Perkin Elmer were used as recommended by the manufacturer, varying the tyramide reagent from 1:50 to 1:200. M.O.M. blocking reagent (Vector Labs) was used for murine monoclonal antibodies used on mouse tissue or alternatively directly conjugated antibodies were made with the Zenon mouse IgG labeling kits (Invitrogen).

Statistical Analysis.

GraphPad Prism 5 software was used to calculate mean and standard deviation (SD) for experiments performed in triplicate. Numerical data were log-transformed when appropriate and analyzed by analysis of variance (ANOVA) (two-tailed). Post-hoc analyses were performed using Bonferroni's or Dunnett's corrections when appropriate. Non-parametric data were analyzed by the Kruskal-Wallis method with Dunn's correction for multiple analyses when appropriate. Categorical data were analyzed by w2 analysis after generation of contingency tables (Excel; Microsoft, Redmond, Wash.).

Example 1

Intravenous Administration of Human Recombinant TNFα Allows Plasma Proteins and Viral Particles to Accumulate in Tumours EL4 cells were allowed to form tumours in SCID mice. To compare permeability of tumour vasculature in 1 µg TNF-treated animals versus controls, Evans Blue was administered intravenously to mice, as set out above. FIG. 1A clearly shows that the Evans Blue dye accumulates in the tumour xenografts, but not in the control mice that were treated only with PBS.

To assess distribution of adenovirus in 1 µg TNF-treated animals versus controls, oncolytic adenovirus was injected intravascularly when tumours were 100 mm³ and the relative distribution was assessed by hexon staining and quantitative polymerase chain reaction measurement of viral DNA. Three controls were also used. As shown in FIG. 1B, TNF injection increased the accumulation of viral particles in tumours by three orders of magnitude. Angiotensin II [A2] and combrestatin (OXI4503) have both been reported to increase tumour vessel permeability, but the increases were small compared to TNF.

As shown in FIG. 1C, the administration of TNF increased the accumulation of virus in a dose-dependent manner. Virus accumulation in the tumour was compared to that in the liver and in the spleen. At the dose of 1 µg TNF, there was enrichment in the tumour over the liver.

Example 2

Expression of VCAM-1 in Human Brain Metastases and in a Murine Model of Brain Metastasis Brain tissue from 12 patients with brain metastases has been obtained and analysed for VCAM-1 expression. The majority of these samples were from fully established metastases of surgical material (diagnosed on CT/MRI). VCAM-1 was variably expressed in the endothelial cells of these solid metastases (FIGS. 2, C and E), and this expression was stronger when the metastases elicited an inflammatory response (FIG. 2E). Interestingly, one metastasis also showed strong staining of the tumour cell membranes (FIG. 2D). Although it is difficult to obtain tissue from early stage brain metastases, given that these cannot currently be diagnosed, we were able to find a few such samples. Importantly, in these samples very strong VCAM-1 expression was found in vessels adjacent to perivascular micrometastases (e.g. FIG. 2F-G). These data are consistent with VCAM-1 being upregulated in association with early metastasis in the human brain.

VCAM-1 expression associated with tumour vasculature was also shown in a murine model of brain metastasis. Female balb/c mice were injected intracardially with $10^4$ 4T1-GFP tumour cells, a metastatic murine mammary carcinoma cell line, and immunofluorescent images were subsequently taken through the resultant brain metastases. In both of the observed metastases upregulation of VCAM-1 expression is clearly evident on the vessels surrounding the tumours. However, the area of VCAM-1 expression also extends further away from the tumours, and thus provides an "amplified" signal for tumour detection. VCAM-1 expression has been detected at days 5 and 10 after intracardiac injection, and studies are on-going to determine the earliest time point for detection. Focal microglial activation is detectable from day 3 at the tumour site, indicating early upregulation of inflammatory cascades. Thus, it is likely that VCAM-1 upregulation begins very early in metastasis development.

Example 3

Changes in Blood Vessel Permeability in Brain Metastasis

Experimental brain metastases were established by intracardiac injection of $10^5$ tumour cells. After 7 days, when the tumour metastases had established themselves but there is no BBB breakdown, the mice were injected intravenously with either 1 µg recombinant human TNF or vehicle. Animals were killed 2 hours or 24 hours after the TNF or vehicle injections. Thirty minutes before being killed, the animals were injected intravenously with type II HRP (Sigma Chemical Co., St Louis, USA), 104 U/kg, as a tracer of increased BBB permeability. The animals were then perfusion-fixed. Coronal, free-floating, sections were cut for HRP localization by a modified Hanker-Yates method (Perry and Linden, 1982). HRP has been used extensively as a tracer of altered vessel permeability, and does not increase endothelial transport during normal conditions.

All animals were anaesthetized with sodium pentobarbitone and then transcardially perfused with 10 ml of saline (heparinized) followed by 50 ml of Karnovsky's fixative (1.25% gluteraldehyde and 1.25% paraformaldehyde in phosphate buffer). The brain was removed, fixed for a further 4 h, and cryoprotected in 30% sucrose overnight at 4° C. before being embedded in Tissue-Tek (Miles Inc, Elkhart, USA) and quickly frozen in liquid nitrogen. Tumours were identified by cellular morphology on adjacent cresyl violet-stained sections.

Changes in vessel permeability to HRP, which is normally excluded from the brain were observed following injections of cytokine at 2 hours only and only in the regions associated with micrometastasis (see FIG. 4). Here TNF was given peripherally (1 µg), but breakdown of the blood brain barrier only occurs at the site of the micrometastasis and is clearly as brown foci indicated by the arrows. No breakdown was evident anywhere in the brain (including meningies) at 24 hours and TNF did not have a global effect on the BBB.

---

The invention claimed is:

1. A method of detecting a metastatic brain tumor behind an intact blood brain barrier in a patient who has a peripheral primary tumor, said method comprising systemically administering to the patient a signal generating agent and a proinflammatory cytokine, wherein the proinflammatory cytokine binds specifically to TNF-receptor TNFR-1 or TNFR-2, and wherein the proinflammatory cytokine is administered at a sub-therapeutic dose for the treatment of tumors, wherein the sub-therapeutic dose of the proinflammatory cytokine is not cytotoxic to a brain tumor and/or does not cause tumor regression when administered systemically, wherein the sub-therapeutic dose of the proinflammatory cytokine permeabilizes pre-existing host vasculature adjacent to the metastatic brain tumor and disrupts the intact blood brain barrier of the metastatic brain tumor to improve access of the signal generating agent to the metastatic brain tumor, and imaging the brain of the patient to detect the tumor, wherein the metastatic brain tumor is not detectable by imaging in the absence of the pro-inflammatory cytokine.

2. The method of claim 1, wherein said permeabilization is specific to tumor vasculature and is transient.

3. The method of claim 1, wherein said proinflammatory cytokine is selected from TNF and lymphotoxin α.

4. The method of claim 1, wherein the proinflammatory cytokine comprises
   (i) an amino acid sequence as set forth in SEQ ID NO:1 or 2, or
   (ii) an amino acid sequence with at least 95% identity to said sequence in (i),
   wherein the proinflammatory cytokine promotes an inflammatory response, which response is inhibited by IL-10.

5. The method of claim 1, wherein said patient is a human.

6. The method of claim 1, wherein said proinflammatory cytokine is administered parenterally, enterally or intravenously.

7. The method of claim 1, wherein said proinflammatory cytokine is formulated with a carrier protein.

8. The method of claim 1, wherein said signal generating agent is selected from a gadolinium-based compound and an iron oxide contrast agent.

9. The method of claim 1, wherein said proinflammatory cytokine is administered to said patient in a single dose of 10-150 μg/m2.

10. The method of claim 1, wherein said proinflammatory cytokine is administered to said patient at a dose which is less than the maximum tolerated dose (MTD).

11. A method of treating a human patient who has a metastasizing peripheral primary tumor capable of metastasizing to the brain, said method comprising systemically administering to said human patient an anti-cancer agent and a proinflammatory cytokine, wherein the pro-inflammatory cytokine binds specifically to TNF-receptor TNFR-1 or TNFR-2, and wherein the pro-inflammatory cytokine is administered at a sub-therapeutic dose for the treatment of tumors, wherein the sub-therapeutic dose of the proinflammatory cytokine is not cytotoxic to a brain tumor and/or does not cause tumor regression when administered systemically and is less than the maximum tolerated dose (MTD), and wherein the sub-therapeutic dose of the proinflammatory cytokine transiently permeabilizes pre-existing host vasculature adjacent to any metastatic brain tumor present behind an intact blood brain barrier in said human patient and disrupts the intact blood brain barrier of the metastatic brain tumor to improve access of the anticancer agent to the metastatic brain tumor for treatment thereof, and wherein, in the absence of any metastatic brain tumor present behind an intact brain barrier, the sub-therapeutic dose of the proinflammatory cytokine does not permeabilize pre-existing non-tumor host vasculature.

12. The method of claim 11, wherein said anticancer agent is selected from a chemotherapeutic agent, an oncolytic virus, a monoclonal antibody, and an exosome containing a therapeutic nucleic acid molecule.

13. The method of claim 12, wherein said chemotherapeutic agent is selected from lapatinib, doxorubicin, melphalan, and paclitaxel.

14. The method of claim 11, wherein the patient has not been diagnosed with a metastatic brain tumour.

15. The method of claim 11, wherein the patient has been diagnosed with a metastatic brain tumour.

16. The method of claim 11, wherein said proinflammatory cytokine is selected from TNF and lymphotoxin α.

17. The method of claim 11, wherein the proinflammatory cytokine comprises
   (i) an amino acid sequence as set forth in SEQ ID NO:1 or 2, or
   (ii) an amino acid sequence with at least 95% identity to said sequence in (i),
   wherein the proinflammatory cytokine promotes an inflammatory response, which response is inhibited by IL-10.

18. The method of claim 11, wherein said proinflammatory cytokine is formulated with a carrier protein.

19. A method of treating a patient who has a metastasizing peripheral primary tumor capable of metastasizing to the brain, said method comprising systemically administering to said patient an anti-cancer agent and a proinflammatory cytokine, wherein the pro-inflammatory cytokine binds specifically to TNF-receptor TNFR-1 or TNFR-2, and wherein the pro-inflammatory cytokine is administered in an amount of 0.5-200 μg/m2 wherein said amount is a sub-therapeutic dose for the treatment of tumors which is not cytotoxic to a brain tumor and/or does not cause tumor regression when administered systemically, and wherein the sub-therapeutic dose of the proinflammatory cytokine transiently permeabilizes pre-existing host vasculature adjacent to any metastatic brain tumor present behind an intact blood brain barrier in said patient and disrupts the intact blood brain barrier of the metastatic brain tumor to improve access of the anti-cancer agent to the metastatic brain tumor for treatment thereof, and wherein, in the absence of any metastatic brain tumor present behind an intact brain barrier, the sub-therapeutic dose of the proinflammatory cytokine does not permeabilize pre-existing non-tumor host vasculature.

20. The method of claim 19, wherein said patient is a human.

21. The method of claim 19, wherein said proinflammatory cytokine is administered parenterally, enterally or intravenously.

22. The method of claim 19, wherein said proinflammatory cytokine is administered to said patient in an amount of 5-200 μg/m2.

23. The method of claim 19, wherein said proinflammatory cytokine is administered to said patient in an amount of 10-150 μg/m2.

24. A method of imaging the brain of a patient who has a peripheral primary tumor, said method comprising
systemically administering to the patient a signal generating agent and a proinflammatory cytokine, wherein the proinflammatory cytokine binds specifically to TNF-receptor TNFR-1 or TNFR-2, and wherein the proinflammatory cytokine is administered at a sub-therapeutic dose for the treatment of tumors, wherein the sub-therapeutic dose of the proinflammatory cytokine is not cytotoxic to a brain tumor and/or does not cause tumor regression when administered systemically, wherein the sub-therapeutic dose of the proinflammatory cytokine improves access of the signal generating agent to the brain, and
imaging the brain of the patient, and optionally detecting a metastatic brain tumor that is not detectable by imaging in the absence of the pro-inflammatory cytokine.

25. The method of claim 24, wherein said proinflammatory cytokine is administered to said patient in an amount of 0.5-200 μg/m2.

26. The method of claim 24, wherein said proinflammatory cytokine is administered to said patient in an amount of 5-200 μg/m2.

27. A method of treating a human patient who has a metastasizing peripheral primary tumor, said method comprising
systemically administering to said human patient an anti-cancer agent and a proinflammatory cytokine, wherein the pro-inflammatory cytokine binds specifically to TNF-receptor TNFR-1 or TNFR-2, and wherein the pro-inflammatory cytokine is administered at a sub-therapeutic dose for the treatment of tumors, wherein the sub-therapeutic dose of the proinflammatory cytokine is not cytotoxic to a brain tumor and/or does not cause tumor regression when administered systemically and is less than the maximum tolerated dose (MTD), and wherein the sub-therapeutic dose of the proinflammatory cytokine transiently permeabilizes pre-existing host vasculature adjacent to any metastatic brain tumor present behind an intact blood brain barrier in said human patient and disrupts the intact blood brain barrier of the metastatic brain tumor to improve access of the anticancer agent to the metastatic brain tumor for treatment thereof, and wherein, in the absence of any metastatic brain tumor present behind an intact blood brain barrier, the sub-therapeutic dose of the proinflammatory cytokine does not permeabilize pre-existing non-tumor host vasculature.

28. A method of treating a patient who has a metastasizing peripheral primary tumor, said method comprising
systemically administering to said patient an anti-cancer agent and a proinflammatory cytokine, wherein the pro-inflammatory cytokine binds specifically to TNF-receptor TNFR-1 or TNFR-2, and wherein the pro-inflammatory cytokine is administered in an amount of 0.5-200 μg/m2 wherein said amount is a sub-therapeutic dose for the treatment of tumors which is not cytotoxic to a brain tumor and/or does not cause tumor regression when administered systemically, and wherein the sub-therapeutic dose of the proinflammatory cytokine transiently permeabilizes pre-existing host vasculature adjacent to any metastatic brain tumor present behind an intact blood brain barrier in said patient and disrupts the intact blood brain barrier of the metastatic brain tumor to improve access of the anti-cancer agent to the metastatic brain tumor for treatment thereof, and wherein, in the absence of any metastatic brain tumor present behind an intact brain barrier, the sub-therapeutic dose of the proinflammatory cytokine does not permeabilize non-tumor host vasculature.

* * * * *